US011779699B2

(12) United States Patent
Pedroni et al.

(10) Patent No.: US 11,779,699 B2
(45) Date of Patent: Oct. 10, 2023

(54) MICROPUMP

(71) Applicant: Lynntech, Inc., College Station, TX (US)

(72) Inventors: Jesse Pedroni, Castle Rock, CO (US); Jibi Varughese, Eindhoven (NL); Grayson Ridge, Highlands Ranch, CO (US); Graham Weeks, College Station, TX (US); Alex Moreland, College Station, TX (US); Jonathan Presley, College Station, TX (US); Jonathan A. Reeh, College Station, TX (US); Tiffany Jefferson, The Woodlands, TX (US); Seth Berry, Bryan, TX (US); Seth Cocking, Sugar Land, TX (US); Justin McIntire, College Station, TX (US); Jady Stevens, Bryan, TX (US); Chris Hadley, Bryan, TX (US); John Zbranek, College Station, TX (US); Rebecca Berger, Bryan, TX (US); Kacey G. Ortiz, College Station, TX (US); Geoffrey Duncan Hitchens, Allen, TX (US); Ashwin Balasubramanian, The Woodlands, TX (US)

(73) Assignee: LYNNTECH, INC., College Station, TX (US)

( * ) Notice: Subject to any disclaimer, the term of this patent is extended or adjusted under 35 U.S.C. 154(b) by 393 days.

(21) Appl. No.: 17/011,749

(22) Filed: Sep. 3, 2020

(65) Prior Publication Data

US 2021/0060237 A1 Mar. 4, 2021
US 2022/0080111 A2 Mar. 17, 2022
US 2022/0193329 A2 Jun. 23, 2022

Related U.S. Application Data

(60) Provisional application No. 62/895,575, filed on Sep. 4, 2019.

(51) Int. Cl.
*A61M 5/168* (2006.01)
*A61M 5/145* (2006.01)
(Continued)

(52) U.S. Cl.
CPC ...... *A61M 5/1454* (2013.01); *A61M 5/16809* (2013.01); *A61M 5/16886* (2013.01);
(Continued)

(58) Field of Classification Search
CPC .......... A61M 5/16804; A61M 5/16809; A61M 2005/14268
See application file for complete search history.

(56) References Cited

U.S. PATENT DOCUMENTS 4,080,967 A 3/1978 O'Leary
4,424,720 A 1/1984 Bucchianeri
(Continued)

FOREIGN PATENT DOCUMENTS

WO 1990015632 12/1990
WO 2012040528 A1 3/2012
WO 2016089772 A1 6/2016

OTHER PUBLICATIONS

Alaris Medical Systems, Inc., MedSystem III® Infusion System with Advanced Dose Rate Calculation and Drug List Editor, User Manual, 2002, 66 pp.

*Primary Examiner* — Emily L Schmidt
(74) *Attorney, Agent, or Firm* — Edwin S. Flores; Chalker Flores, LLP

(57) ABSTRACT

A pump including a disposable component including a disposable component inlet port coupled to a first disposable conduit in fluid communication with a fluid medium source, wherein the first disposable conduit includes a disposable piston pump assembly and a disposable bubble eliminator, and the first disposable conduit is in fluid communication
(Continued)

with a disposable component outlet port, wherein the disposable bubble eliminator is in fluid communication with a lumen of the first disposable conduit and is operable to reduce a gas content of a fluid medium; wherein the disposable piston pump assembly is operable to pump the fluid medium from the disposable component inlet port, through the first disposable conduit and the disposable bubble eliminator, to the disposable component outlet port; and a reusable component including a reusable movable stage operable to compress the disposable piston pump assembly; and a reusable mechanical actuator operable to drive the movable stage.

14 Claims, 17 Drawing Sheets

(51) Int. Cl.
  *A61M 5/50* (2006.01)
  *A61M 5/142* (2006.01)
(52) U.S. Cl.
  CPC ........... *A61M 2005/14268* (2013.01); *A61M 2005/5046* (2013.01); *A61M 2205/3334* (2013.01); *A61M 2205/505* (2013.01); *A61M 2205/8206* (2013.01); *A61M 2205/8262* (2013.01)

(56) References Cited

U.S. PATENT DOCUMENTS

| | | |
|---|---|---|
| 4,515,591 A | 5/1985 | Hemmerich et al. |
| 5,006,050 A | 4/1991 | Cooke et al. |
| 7,201,746 B2 | 4/2007 | Olsen |
| 8,152,477 B2 | 4/2012 | Anex et al. |
| 9,107,995 B2 | 8/2015 | Pang et al. |
| 9,402,950 B2 | 8/2016 | Dilanni et al. |
| 9,968,733 B2 | 5/2018 | Haase et al. |
| 2002/0169439 A1* | 11/2002 | Flaherty ................ A61P 9/10 604/891.1 |
| 2006/0173418 A1 | 8/2006 | Rinaudo et al. |
| 2008/0287874 A1 | 11/2008 | Elmouelhi |
| 2011/0137255 A1 | 6/2011 | Nielsen et al. |
| 2011/0218516 A1* | 9/2011 | Grigorov .......... A61M 5/14248 222/105 |
| 2011/0275987 A1 | 11/2011 | Caffey et al. |
| 2012/0004602 A1* | 1/2012 | Hanson ................ A61M 5/172 604/67 |
| 2012/0172800 A1* | 7/2012 | Dudar ..................... A61M 5/38 604/123 |
| 2014/0322037 A1 | 10/2014 | Lindekleiv |
| 2019/0275241 A1* | 9/2019 | Ring ................. A61M 5/16813 |

\* cited by examiner

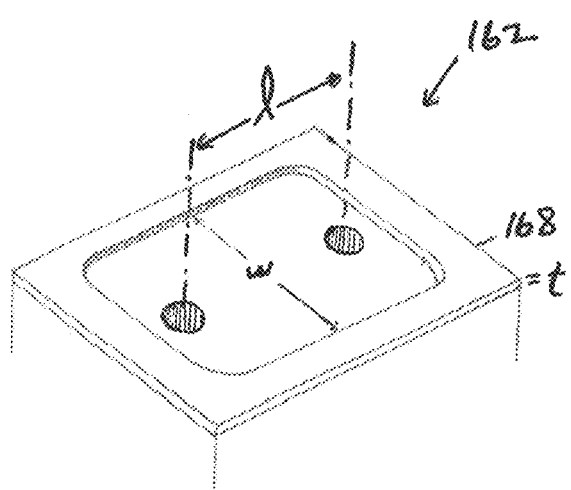 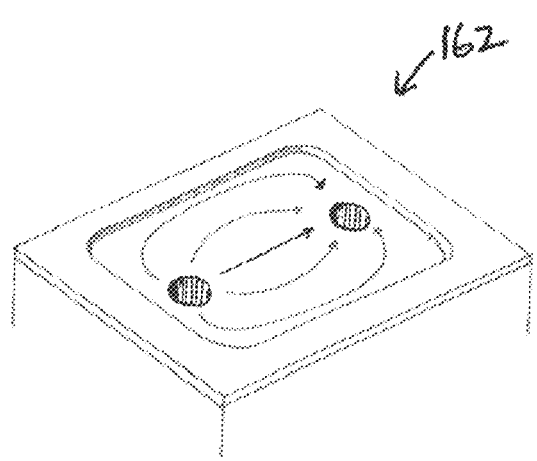
FIG. 7A
FIG. 7B

MICROPUMP

CROSS-REFERENCE TO RELATED APPLICATIONS

This application claims priority to U.S. Provisional Application Ser. No. 62/895,575, filed Sep. 4, 2019, the entire contents of which are incorporated herein by reference.

STATEMENT OF FEDERALLY FUNDED RESEARCH

This invention was made with government support under W81XWH-16-C-0035 awarded by the US Army Medical Research and Materiel Command. The government has certain rights in the invention.

TECHNICAL FIELD OF THE INVENTION

The present invention relates in general to the field of infusion pumps. In particular, the present invention relates to an infusion pump with a disposable component and a capacity to remove gases from a fluid to be infused.

BACKGROUND OF THE INVENTION

Infusion pumps are commonly used to infuse substances such as blood and medications into patients. Existing infusion pumps generally require fixed power sources. Many existing infusion pumps also require costly and time-consuming cleaning between uses. In addition, many existing infusion pumps lack a capacity to detect and minimize the occurrence of gases in the fluid to be infused.

The prior art includes U.S. Pat. No. 10,384,004, to Zhu, which is said to disclose processes for operating an infusion pump for pumping fluid though an administration set at a constant flow rate; wherein the pump includes a pumping mechanism for pumping fluid and operates at a pulse frequency, and a controller controls the pulse frequency; wherein the pump has one or more sensors configured for measuring at least one characteristic value relating to a status of the infusion pump; wherein the controller is configured for causing the pumping mechanism to operate at a first pulse frequency, and the one or more sensors measure the characteristic value; and wherein, when the measured characteristic value meets a threshold value, the controller causes the pumping mechanism to operate at a second pulse frequency different from the first pulse frequency.

In addition, the prior art includes U.S. Pat. No. 10,387,624, to Jedwab, et al., which is said to disclose an infusion pump having a control unit and a graphical user interface functionally connected to the controller, wherein the control unit is designed to receive at least two sensor signals out of the following group of sensors: cassette presence sensor, door sensor, pressure sensor, air presence sensor, motor sensor, flow rate sensor, wherein the control unit is designed to detect an error state based on the analysis of the at least two supplied sensor signals, wherein the control unit is designed to associate a degree of severity out of at least two degrees of severities based on the processing of the supplied sensor signals, and wherein the control unit is designed to control a color of the display of the graphical user interface to be displayed, wherein a different color is associated with each degree of severity as well as with a non-error state.

SUMMARY OF THE INVENTION

In some embodiments of the disclosure, a pump is disclosed as including a disposable component including a disposable component inlet port coupled to a first disposable conduit in fluid communication with a fluid medium source, wherein the first disposable conduit includes a disposable piston pump assembly and a disposable bubble eliminator, and the first disposable conduit is in fluid communication with a disposable component outlet port, wherein the disposable bubble eliminator is in fluid communication with a lumen of the first disposable conduit and is operable to reduce a gas content of a fluid medium; wherein the disposable piston pump assembly is operable to pump the fluid medium from the disposable component inlet port, through the first disposable conduit and the disposable bubble eliminator, to the disposable component outlet port; and a reusable component including a reusable movable stage operable to compress the disposable piston pump assembly; and a reusable mechanical actuator operable to drive the movable stage. In one aspect, the disposable component further includes a first one-way outlet valve disposed in the first disposable conduit between the piston assembly and the disposable bubble eliminator and operable to prevent the fluid medium from flowing from the disposable bubble eliminator to the disposable piston pump assembly; a disposable flow meter positioned to measure a fluid flow through the first disposable conduit; and a second one-way outlet valve disposed in the second disposable conduit between the disposable bubble eliminator and the disposable flow meter and operable to prevent the fluid medium from flowing from the disposable flow meter to the disposable bubble eliminator; and the reusable component further includes a reusable reception tunnel configured to receive at least a portion of the first disposable conduit; a reusable inlet valve operable to close the first disposable conduit when the at least a portion of the first disposable conduit is disposed in the reusable reception tunnel; a reusable flow meter connector operable to connect to the disposable flow meter and to convey data from the disposable flow meter; and a reusable bubble detector. In another aspect, the reusable inlet valve is a one-way valve or a pinch valve. In another aspect, the disposable piston pump assembly includes a piston barrel including a pump chamber in fluid communication with the first disposable conduit; a plunger slidably disposed within the piston barrel below the pump chamber; a piston rod attached to the plunger opposite the pump chamber; a spring cap attached to the piston rod; and a spring disposed around an exterior of the piston barrel and attached at an upper end of the spring to the exterior of the piston barrel and at a lower end of the spring to the spring cap, wherein the spring is disposed to store energy when the plunger, the piston rod, and the spring cap are moved into the piston barrel and is disposed not to store energy when the plunger is at the lower end of the pump chamber; wherein the reusable movable stage is disposed to move the plunger upward in the piston barrel and the spring is disposed to move the plunger downward in the pump chamber. In another aspect, the disposable bubble eliminator is in fluid communication with the disposable piston pump assembly and the disposable flow meter and includes a vent through which gas in the fluid medium may escape the disposable bubble eliminator to the atmosphere when pressure higher than atmospheric pressure is maintained in the disposable bubble eliminator. In another aspect, the disposable component further includes a disposable position measurement device to detect an alignment of the disposable component with the reusable component when assembled together. In another aspect, the reusable bubble detector includes a reusable bubble detector conduit in fluid communication with the disposable component outlet port when the disposable component and the reusable component are assembled together; and a reusable ultrasonic sensor to detect gas in the fluid medium, disposed outside the reusable bubble detector conduit. In another aspect, the reusable component further includes an internal electric battery or electrical connections configured to connect to an external electrical power source or both. In another aspect, the reusable component further includes an internal power management system or power management connections configured to connect to an external power management system or both. In another aspect, the reusable component further includes an integral control panel or control panel connections configured to connect to an external control panel or both. In another aspect, the reusable component further includes a screen interface or screen interface connections configured to connect to an external screen interface or both. In another aspect, the disposable component is enclosed in a disposable housing or the reusable component is disclosed in a reusable housing or both.

In some embodiments of the disclosure, a method of pumping a fluid is disclosed as including providing a disposable pump component including a disposable component inlet port coupled to a first disposable conduit in fluid communication with a fluid medium source, wherein the first disposable conduit includes a disposable piston pump assembly and a disposable bubble eliminator, and the first disposable conduit is in fluid communication with a disposable component outlet port, wherein the disposable bubble eliminator is in fluid communication with a lumen of the first disposable conduit and is operable to reduce a gas content of a fluid medium, and wherein the disposable piston pump assembly is operable to pump the fluid medium from the disposable component inlet port, through the first disposable conduit and the disposable bubble eliminator, to the disposable component outlet port; and connecting the disposable component to a reusable component including a reusable movable stage operable to compress the disposable piston pump assembly; and a reusable mechanical actuator operable to drive the movable stage.

In some embodiments of the disclosure, a method of pumping a fluid medium is disclosed as including receiving the fluid medium from a fluid medium source into a conduit; drawing the fluid medium into a disposable piston pump assembly in the conduit, the conduit further including a disposable bubble eliminator operable to vent gas from the fluid medium within the disposable bubble eliminator; flowing the fluid medium through a disposable flow meter; measuring a flow rate of the fluid medium; discharging the fluid medium into a reusable bubble detector; detecting residual gas in the fluid medium; if less than a preselected amount of gas is detected, discharging the fluid medium from the reusable bubble detector. In one aspect, the disposable piston pump assembly includes a piston barrel including a pump chamber in fluid communication with the first disposable conduit; a plunger slidably disposed within the piston barrel below the pump chamber; a piston rod attached to the plunger opposite the pump chamber; a spring cap attached to the piston rod; and a spring disposed around an exterior of the piston barrel and attached at an upper end of the spring to the exterior of the piston barrel and at a lower end of the spring to the spring cap, wherein the spring is disposed to store energy when the plunger, the piston rod, and the spring cap are moved from a lower end of the piston barrel and is disposed not to store energy when the plunger is at the lower end of the pump chamber; wherein the reusable movable stage is disposed to move the plunger into the pump chamber and the spring is disposed to move the plunger out of the pump chamber. In another aspect, the disposable bubble eliminator is in fluid communication with the disposable piston pump assembly and the disposable flow meter and includes a vent through which gas in the fluid medium may escape the disposable bubble eliminator to the atmosphere when pressure higher than atmospheric pressure is maintained in the disposable bubble eliminator. In another aspect, the method further includes detecting an alignment of the disposable component with the reusable component when assembled together. In another aspect, the reusable bubble detector includes a reusable bubble detector conduit in fluid communication with the disposable component outlet port when the disposable component and the reusable component are assembled together; and a reusable ultrasonic sensor to detect gas in the fluid medium, disposed outside the reusable bubble detector conduit. In another aspect, the method further includes supplying electrical power from an internal electric battery or an external electrical power source. In another aspect, the method further includes managing electrical power with an internal power management system or an external power management system. In another aspect, the method further includes supplying an integral screen interface or an external screen interface.

In some embodiments of the disclosure, a kit is disclosed as including a disposable component including a disposable component inlet port coupled to a first disposable conduit in fluid communication with a fluid medium source, wherein the first disposable conduit includes a disposable piston pump assembly and a disposable bubble eliminator, and the first disposable conduit is in fluid communication with a disposable component outlet port, wherein the disposable bubble eliminator is in fluid communication with a lumen of the first disposable conduit and is operable to reduce a gas content of a fluid medium; wherein the disposable piston pump assembly is operable to pump the fluid medium from the disposable component inlet port, through the first disposable conduit and the disposable bubble eliminator, to the disposable component outlet port; and a reusable component including a reusable movable stage operable to compress the disposable piston pump assembly; and a reusable mechanical actuator operable to drive the movable stage. In one aspect, the disposable component further includes a first one-way outlet valve disposed in the first disposable conduit between the piston assembly and the disposable bubble eliminator and operable to prevent the fluid medium from flowing from the disposable bubble eliminator to the disposable piston pump assembly; a second disposable conduit that places the disposable bubble eliminator in fluid communication with a disposable flow meter; a second one-way outlet valve disposed in the second disposable conduit between the disposable bubble eliminator and the disposable flow meter and operable to prevent the fluid medium from flowing from the disposable flow meter to the disposable bubble eliminator; and the reusable component further includes a reusable reception tunnel configured to receive at least a portion of the first disposable conduit; a reusable inlet valve operable to close the first disposable conduit when the at least a portion of the first disposable conduit is disposed in the reusable reception tunnel; a reusable flow meter connector operable to connect to the disposable flow meter and to convey data from the disposable flow meter; and a reusable bubble detector. In another aspect, the reusable inlet valve is a one-way valve or a pinch valve. In another aspect, the disposable piston pump assembly includes a piston barrel including a pump chamber in fluid communication with the first disposable conduit; a plunger slidably disposed within the piston barrel below the pump chamber; a piston rod attached to the plunger opposite the pump chamber; a spring cap attached to the piston rod; and a spring disposed around an exterior of the piston barrel and attached at an upper end of the spring to the exterior of the piston barrel and at a lower end of the spring to the spring cap, wherein the spring is disposed to store energy when the plunger, the piston rod, and the spring cap are moved into the piston barrel and is disposed not to store energy when the plunger is at the lower end of the pump chamber; wherein the reusable movable stage is disposed to move the plunger upward in the piston barrel and the spring is disposed to move the plunger downward in the pump chamber. In another aspect, the disposable bubble eliminator is in fluid communication with the disposable piston pump assembly and the disposable flow meter and includes a vent through which gas in the fluid medium may escape the disposable bubble eliminator to the atmosphere when pressure higher than atmospheric pressure is maintained in the disposable bubble eliminator. In another aspect, the disposable component further includes a disposable position measurement device to detect an alignment of the disposable component with the reusable component when assembled together. In another aspect, the reusable bubble detector includes a reusable bubble detector conduit in fluid communication with the disposable component outlet port when the disposable component and the reusable component are assembled together; and a reusable ultrasonic sensor to detect gas in the fluid medium, disposed outside the reusable bubble detector conduit. In another aspect, the reusable component further includes an internal electric battery or electrical connections configured to connect to an external electrical power source or both. In another aspect, the reusable component further includes an internal power management system or power management connections configured to connect to an external power management system or both. In another aspect, the reusable component further includes an integral control panel or control panel connections configured to connect to an external control panel or both. In another aspect, the reusable component further includes a screen interface or screen interface connections configured to connect to an external screen interface or both. In another aspect, the disposable component is enclosed in a disposable housing or the reusable component is disclosed in a reusable housing or both.

BRIEF DESCRIPTION OF THE DRAWINGS

For a more complete understanding of the features and advantages of the present invention, reference is now made to the detailed description of the invention along with the accompanying figures, in which:

FIGS. 7A and 7B show the bubble eliminator chamber and the approximate fluid flow lines within it, respectively.

DETAILED DESCRIPTION OF THE INVENTION

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Infusion pumps are commonly used to infuse substances such as blood and medications into patients. They often need to be used untethered from electrical power connections, such as in ambulatory situations, where operation by internal battery power is convenient or necessary. Also, it is desirable to have a pump comprising certain disposable components which, for patient safety reasons, are discarded and replaced frequently. It is desirable that a pump have the operability to detect and minimize occurrence of gases in the fluid to be infused, to ensure correct direction of fluid flow, to prevent uncontrolled flow of fluid to be infused, and to control the rate of flow of fluid that is being infused, with accurate measurement and verification of the rate of fluid flow.

Figure 1:
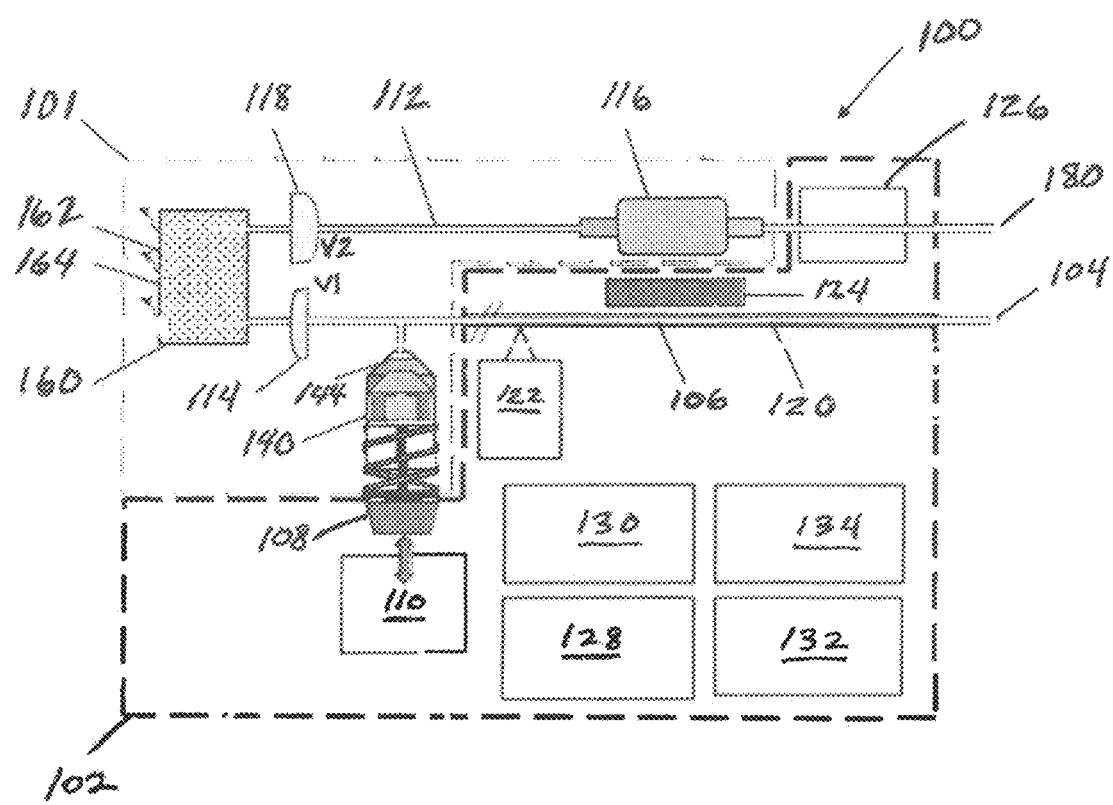
FIG. 1 shows the disposable component and the reusable component of the pump attached together.

An embodiment of the present invention, a pump 100 for achieving controllable flow, is depicted in FIG. 1. The invention includes a fluid flow path that is defined by multiple disposable parts and systems. The disposable fluid flow path comes into contact with fluids, such as intravenous delivery fluids, drug solutions, blood products, and solutions of bioactive agents. The disposable parts are housed by a disposable component 101.

The invention includes reusable parts and systems that do not come into contact with fluids. The reusable parts and systems are durable and function multiple times with a plurality of different disposable components. In one embodiment, the reusable parts and systems are housed by a reusable component 102. In some embodiments, the parts used to achieve conversion of electrical energy, e.g., electrical energy stored in a battery 128, to mechanical action are housed by the reusable component 102, as are various mechanical drivers, the equipment for monitoring system performance and, the control panel 132 and the edittouch screen 134 for interfacing with a user. The controls to control action and speed motion of the pump are located on the reusable component. It would be wasteful and costly to dispose of these reusable parts because of their sophistication and complexity.

The invention is intended to meet the requirements that a new disposable component 101 be easily connected to and removed from the reusable component 102 and that the disposable and reusable components 101 and 102 respectively, achieve physical, mechanical and electrical integration when attached to each other.

FIG. 1 depicts an embodiment of the present invention, the pump 100, including a disposable component 101 and a reusable component 102, which are shown attached together. The disposable component 101 includes a disposable component inlet port 104 coupled to a first disposable conduit 106 in fluid communication with a fluid medium source (not shown). The first disposable conduit 106 is in fluid communication with a disposable piston pump assembly 140 and a disposable bubble eliminator 160 with bubble eliminator chamber 162. The first disposable conduit 106 is in fluid communication with a disposable component outlet port 180. The disposable bubble eliminator 160 is in fluid communication with a lumen (not shown) of the first disposable conduit 106, and is operable to reduce a gas content of a fluid medium. The disposable piston pump assembly 140 is operable to pump the fluid medium from the disposable component inlet port 104, through the first disposable conduit 106 and the disposable bubble eliminator 160, to the disposable component outlet port 180. The reusable component 102 includes a reusable movable stage 108 operable to compress the disposable piston pump assembly 140 and a reusable mechanical actuator 110 operable to drive the reusable movable stage 108.

The disposable component 101 may further include a second disposable conduit 112 in fluid communication with the disposable bubble eliminator 160 and the disposable component outlet port 180. The disposable component 101 may also include a first one-way outlet valve 114 disposed in the first disposable conduit 106 between the disposable piston pump assembly 140 and the disposable bubble eliminator 160, and operable to prevent the fluid medium from flowing from the disposable bubble eliminator 160 to the disposable piston pump assembly 140. The disposable component 101 may further include a disposable flow meter 116 disposed to measure fluid flow through the second disposable conduit 112. The disposable component 101 may also include a second one-way outlet valve 118 disposed between the disposable bubble eliminator 160 and the disposable flow meter 116 and operable to prevent the fluid medium from flowing from the disposable flow meter 116 to the disposable bubble eliminator 160.

The reusable component 102 may further include a reusable reception tunnel 120 configured to receive at least a portion of the first disposable conduit 106. The reusable component 102 may also include a reusable inlet valve 122 that is operable to close the first disposable conduit 106 when the at least a portion of the first disposable conduit 106 is disposed in the reusable reception tunnel 120. The reusable component 102 may also include a reusable flow meter connector 124 operable to connect to the disposable flow meter 116 and to convey data from the disposable flow meter 116. The reusable component 102 may further include a reusable bubble detector 126. The reusable component 102 may also include an internal electric battery or electrical connections configured to connect to an external electrical power source 128 or both. The reusable component 102 may also include an internal power management system or power management connections configured to connect to an external power management system 130 or both. The reusable component 102 may also include an integral control panel or control panel connections configured to connect to an external control panel 132 or both. The reusable component 102 may also include a screen interface or screen interface connections configured to connect to an external screen interface 134 or both.

Figure 2:
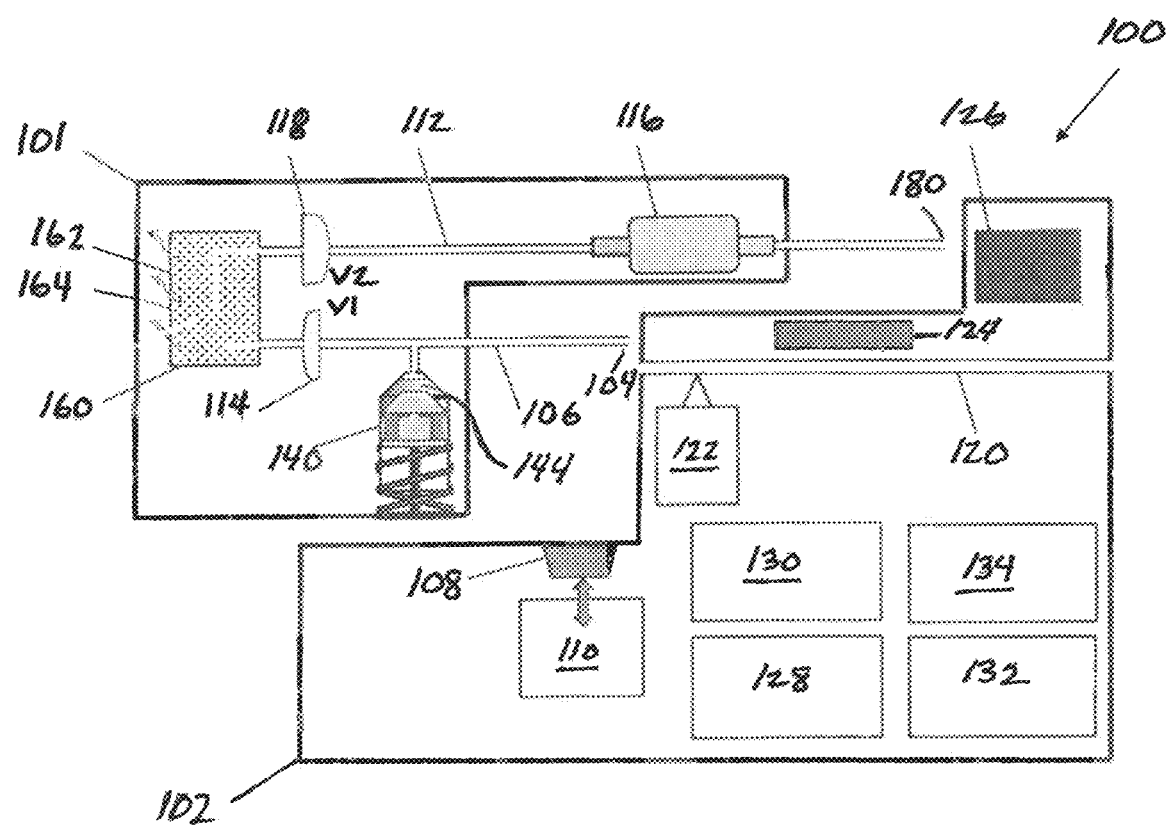
FIG. 2 shows the disposable component and the reusable component of the pump detached from each other.

FIG. 1 depicts the operational configuration of one embodiment of the pump 100, where the reusable component 102 is coupled, physically, mechanically, and electrically to the disposable component 101. FIG. 2 depicts the situation when the disposable and reusable components shown attached in FIG. 1 are disconnected from each other.

The disposable component 101 includes the reciprocating disposable piston pump assembly 140, which is of metallic or polymer construction. The disposable piston pump assembly 140 makes contact with a moveable stage 108 in the reusable component 102. The motion of the reusable moveable stage 108 is driven by the mechanical actuator 110, which is also in the reusable component 102. The reusable mechanical actuator 110 provides the driving force for the forward stroke of the disposable piston pump assembly 140. The parts needed for converting electrical energy stored in the batteries 128 into mechanical actuation are housed in the reusable component 102, since the parts needed for electrical-to-mechanical conversion typically have significant electrical and mechanical complexity.

In the embodiment shown in FIGS. 1 and 2, the fluid path is defined by tubing and valves, consisting of a disposable component inlet port 104, a disposable component outlet port 180, and a piston pump chamber 144. The fluid flow path is defined by tubing and connections of the type used for delivery of intravenous fluids to the body. The parts defining the fluid path are housed in the disposable component 101. The disposable component 101 includes a disposable component inlet port 104 for receiving the fluid and a disposable component outlet port 180 for supplying the fluid to a patient. A controllable disposable piston pump assembly 140, incorporating the piston pump chamber 144, is used for fluid flow from the disposable component inlet port 104 to the outlet port 180. The reusable inlet valve 122 is disposed in proximity to the disposable component inlet port 104. The reusable inlet valve 122 opens and closes the first disposable conduit 106, which may be disposable IV tubing. In the embodiment illustrated, the reusable inlet valve 122 uses, e.g., a pinch valve mechanism. A pinch valve is a component that allows the mechanical pinching of the outside of a tube, where mechanical pressure deforms the tube sufficiently to restrict or stop flow through the tube's internal diameter. Flow resumes when the mechanical pressure to the outside of the tube is released. The benefit of a pinch valve, compared to alternatives such as a solenoid valve, is that the valve's parts and mechanisms do not come in contact with fluid. A pinch valve can be physically mounted, in its entirety, in the reusable component 102, so as not to dispose of it after a single use. The fluid path through the reusable inlet valve is therefore defined by placement of the first disposable conduit 106.

The controllable disposable piston pump assembly 140 is disposed and operated to achieve fluid flow in the direction of the disposable component outlet port 180. In addition to the reusable inlet valve 122 and the disposable piston pump assembly 140, there are two one-way outlet valves (V1 and V2), 114 and 118, respectively, disposed between the disposable piston pump assembly and the disposable component outlet port. The one-way outlet valves V1 114 and V2 118 are part of the disposable component 101. The fluid is pumped in only one direction because the one-way outlet valves V1 114 and V2 118 are normally closed but open in response to fluid pressure. In the embodiment shown in FIG. 1, after fluid is introduced into the pump chamber 144, the reusable inlet valve 122 is closed. As the piston increases the pressure in the pump chamber 144, the output valves V1 114 and V2 118 downstream are forced open, and the fluid flows towards the disposable component outlet port 180. When the pressure drops sufficiently during the retraction stroke, the one-way outlet valves V1 114 and V2 118 close, and the reusable inlet valve 122 is opened to admit more fluid. The two one-way outlet valves V1 114 and V2 118 are passive (not controlled electrically as compared to the inlet valve 122). These valves V1 114 and V2 118 are umbrella-type valves, allowing fluid to flow one direction but not the other. An umbrella valve looks like an umbrella. As the fluid travels in one direction the umbrella valve opens allowing the fluid to pass, but as the fluid tries to reverse direction, the umbrella valve closes and prevents any fluid from traveling towards the inlet.

The embodiment shown in FIGS. 1 and 2 includes a disposable bubble eliminator 160 located between one-way outlet valves V1 114 and V2 118. The disposable bubble eliminator 160 includes a fluid chamber 162. One or more walls of the chamber 162 are formed from a gas permeable porous membrane 164, allowing gas to vent to the external atmosphere. The disposable bubble eliminator 160 is placed in the fluid flow path such that positive pressure conditions are maintained within the bubble eliminator chamber 162 at all times. Operation and orientation of one-way valves V1 114 and V2 118 working in coordination with the disposable piston pump assembly 140, are important in managing the bubble eliminator chamber 162 fluid pressure. The fluid side of the disposable bubble eliminator 160 is always is at a higher pressure than atmospheric during the prime stroke as well as the forward stroke of the disposable piston pump assembly 140.

The embodiment shown in FIGS. 1 and 2 includes the disposable flow meter 116 positioned towards the outlet. The device is suitable for monitoring or measuring the activity and accuracy of the disposable piston pump assembly 140. The disposable flow meter 116 is part of the disposable component 101. An example disposable flow meter is the Sensiron LD 20-2600B. It operates based on a thermal gradient detection, suitable for integration into the disposable component 101. The disposable flow meter 116 is a direct flow measurement device used to monitor gross flow rate error, occlusion, and infiltration and to verify that the pump head is installed properly. The disposable flow meter 116 can measure the flow of all standard IV fluids, drugs formations, as well as blood and other high viscosity fluids. The flow meter may also assist in a free flow prevention algorithm.

In the embodiment shown in FIGS. 1 and 2 the disposable flow meter 116 has the additional purpose of determining correct positioning of the disposable component 101 with respect to the position of the reusable component 102. This informs the user that correct alignment between the components 101 and 102 is achieved, to accomplish physical, mechanical, and electrical coupling prior to pump operation. The flow sensor operates in conjunction with a reusable flow meter connector 124, which is part of the reusable component 102.

The embodiment shown in FIGS. 1 and 2 incorporates a reusable bubble detector 126, which may include an ultrasonic sensor, to detect air-in-line scenarios. Critical to the safety of the patient during a drug, IV fluid, or blood component infusion is the detection of air boluses in the tubing. An example reusable ultrasonic sensor is a Moog LifeGuard Air Bubble Detector. This reusable ultrasonic sensor is a non-wetted component. It uses ultrasonic frequencies to measure the fluid response in the tubing, alerting the operator if bubbles 50-100 uL are present. The sensor is a part of the reusable component 102.

For fluid flow metering, another method is to measure the movement of the piston of the disposable piston pump assembly 140 very accurately and, with electronic feedback control, use that movement to measure the volume of fluid pumped. The timing of the reusable inlet valve 122 and the reusable mechanical actuator 110 thus can be precisely adjusted to provide accurate fluid flow. The one-way outlet valves V1 114 and V2 118 deflection information, available through a transducer, may provide information which is substantially representative of the operational state of the disposable piston pump assembly 140, thereby enabling control of the timing. In addition to control of timing, the outlet flow from the piston valve may include a device that allows detection of occlusion or partial occlusion of outflow from the pump, gas trapped in the disposable piston pump assembly 140, mechanical failure, disconnection of the line to the patient, and exhaustion of fluid supply.

The disposable fluid lines may be packaged with the disposable component 101 in order for ease of installment and replacement. The disposable component 101 connects to the reusable component 102 by single action clips (not shown) to minimize effort of swapping pump heads. The fluid lines will also be compatible with standard IV drugs, as well as blood, plasma, water, etc.

To operate the pump 100, a user interacts with the touch screen 134. The touch screen 134 may give access to a drug library with preset settings that will include flow rates, bolus amounts for a given patients weight for the various drugs. The user has the capability to manually input the flow rate as well as volume in order for custom solutions. The system also has the capability to be continually updated to include or remove drugs and the parameters associated with them.

The packaging of the pump will house all the components within either of the disposable or reusable components, 101 or 102, respectively. The pump parts may have labels and markings permanently displayed consistent with regulatory agency labeling requirements. It may also have the necessary visual and audible alarms and indicators according to the IEC standard for medical pumps indicating various states (end of infusion, occlusion, air-in-line, battery, equipment failure, etc.). The pump 100 has the capability to be controlled and monitored via Wi-Fi/Bluetooth as well as ability to turn off those features for security purposes.

The control board 132 for the pump may contain a processor in order to operate all electrical components. The reusable component 102 may also contain a Power Management System (PMS) 130 voltage balancing and monitoring, H bridges for reversing the polarity of voltage source electrically coupled to the circuitry of the pump actuation mechanism, sensors for component monitoring, and various other electrical components to operate the pump. The control board 132 also has the capability of controlling the magnitude of voltage or current applied to the individual actuators.

Figure 3:
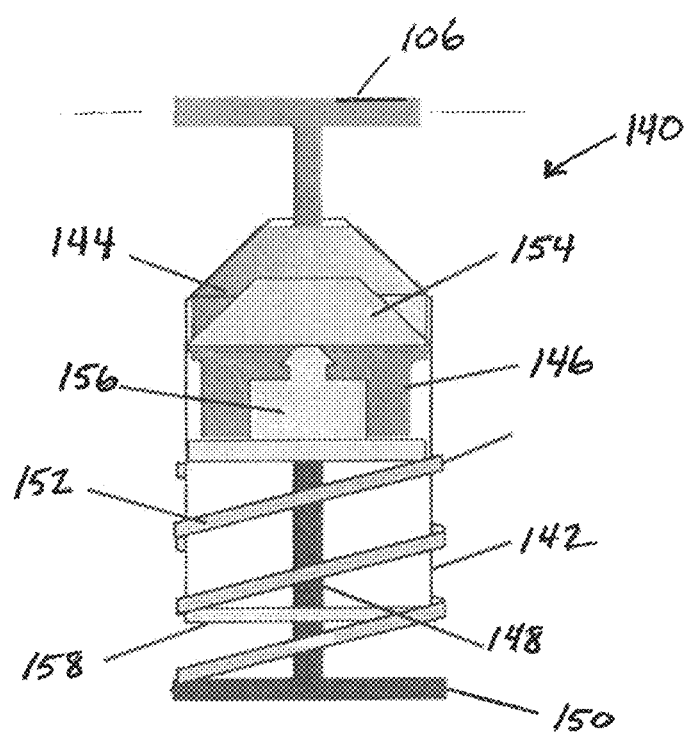
FIG. 3 shows the disposable pump assembly.

Pumping Mechanism. In the embodiment shown in FIGS. 1 and 2, the parts of the pump that contact the fluids that form the fluid flow path are located on the disposable component 101, including the disposable piston pump assembly 140, shown in detail in FIG. 3. The reusable piston pump assembly 140 includes a piston barrel 142 that includes the pump chamber 144 in fluid communication with the first disposable conduit 106, a plunger 146 slidably disposed within the piston barrel 142 below the pump chamber 144, a piston rod 148 attached to the plunger 146 opposite the pump chamber 144, and a spring cap 150 attached to the piston rod 148. Further, the reusable piston pump assembly 140 includes a spring 152 disposed around an exterior of the piston barrel 142 and attached at an upper end of the spring 152 to the exterior of the piston barrel 142 and at a lower end of the spring 152 to the spring cap 150. The spring 152 is disposed to store energy when the plunger 146, the piston rod 148, and the spring cap 150 are moved into the piston barrel 142 and is disposed not to store energy when the plunger 146 is at the lower end of the pump chamber 144. FIG. 3 illustrates disposable piston pump assembly 140 with the spring 152 in a compressed, energy-storing state and the plunger 146 moved into the piston barrel 142. The disposable piston pump assembly 140 may also include a dead volume spacer 154 disposed on the plunger 146 in the pump chamber 144, a plunger insert 156 disposed inside the plunger 144, and a piston hardstop 158 disposed at the bottom of the piston barrel 142.

The disposable piston pump assembly 140 has a flow channel in fluid communication with the disposable component inlet port 104 and the disposable component outlet port 180 via the first disposable conduit 106. One end of the spring 152 is permanently affixed to the disposable piston pump assembly 140 through a permanent attachment mechanism, such as a grooved recess, a weld, solder or adhesive. The opposite end of the spring 152 is permanently connected to the spring cap 150. The permanent attachment of spring 152 to one end of the spring cap 150 is made via a grooved recess, or alternatively by a weld, solder or adhesive. The movement of the plunger 146 is constrained in the forward direction by the piston pump chamber wall at the outlet side. The plunger 146 is constrained in the retracted position by a piston hardstop 158.

Forward movement of the plunger 146 occurs until it reaches a stop point. The disposable piston pump assembly's 140 forward stroke results in the delivery of media from the piston chamber 144. Return or retraction of the plunger 146 occurs under the force of a spring 152, causing the pressure in the piston chamber 144 to fall. The reduced pressure in the piston chamber 144 causes media to flow from the inlet portion 104 through an opening in the piston chamber to refill the piston chamber 144, thus equalizing the pressure between the fluid source and the piston chamber 144. This can be referred to as the retraction, refill, or prime stroke, which prepares the disposable piston pump assembly 140 for its next forward or delivery stroke.

FIGS. 4A-4E show how fluid transfer from the disposable component inlet port 104 to the disposable component outlet port 180 is achieved, involving sequential and coordinated actions involving parts of the disposable component 101 and parts of the reusable component 102. FIGS. 4A-4E depict disposable piston pump assembly 140 including the pump chamber 144, the plunger 146, the spring cap 150, the spring 152, and, in addition, the first disposable conduit 108, the reusable movable stage 108, and the reusable inlet valve 122.

Figure 4A:
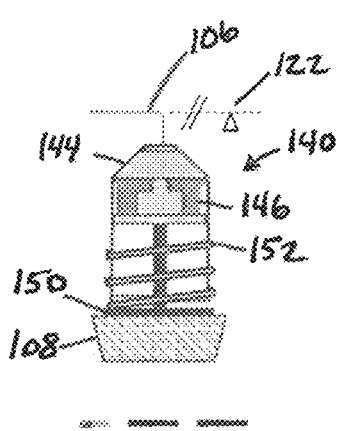
FIGS. 4A-4E show the arrangement of the disposable pump assembly at the completion of the pump stroke, mid-way through the refill stroke, at the completion of the refill stroke, mid-way through the pump stroke, and at the return to the completion of the pump stroke, respectively.

FIG. 4A shows the arrangement of the disposable piston pump assembly 140 at the completion of the forward or pump stroke. The plunger 146 is in the fully forward position. The pump chamber 144 is substantially empty of fluid. The spring 152 is compressed from its resting position. The reusable inlet valve 122 on the first disposable conduit 106 is closed. There is no more fluid flow in the direction of the disposable component outlet port 180. The reusable mechanical actuator 110 of the movable stage is disengaged.

Figure 4B:
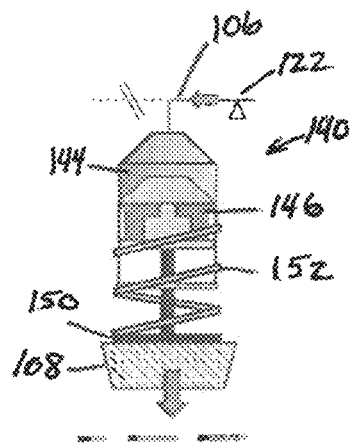

FIG. 4B shows the arrangement mid-way during the retraction or refill stroke of the disposable piston pump assembly 140, where the plunger 146 is partially retracted. During the retraction stroke, the spring 152 undergoes extension which applies a force to the spring cap 150. The mechanical force of the spring 152 acting on the spring cap 150 causes retraction of the plunger 146. Retraction of the plunger 146 results in negative pressure (less than atmospheric) within the pump chamber 144. Fluid flows into the pump chamber 144 from the outlet, due to negative chamber pressure. The refill stroke coincides with mechanical activation to open the reusable inlet valve 122. Due to negative pressure in the pump chamber, one-way outlet valves V1 114 and V2 118 (not shown) are closed, so as to prevent or restrict flow in the direction of the disposable component outlet port 180. In addition to the extension of the spring 152 providing force for plunger 146 retraction, the extension of the spring 152 also applies force to the reusable movable stage 108 causing its retraction. The force to retract the reusable movable stage 108 is applied via the spring cap 150, which makes physical contact with the reusable movable stage 108 via a contact surface. During the retraction stroke, the mechanical actuator connected to the reusable movable stage 108 is disengaged, so the reusable movable stage 108 is free to move in the retraction direction. Thus, during the refill stroke, the disposable component 101 has an energy transfer function, where mechanical energy stored in the spring 152 is transferred to the reusable movable stage 108, which is part of reusable component 102.

Figure 4C:
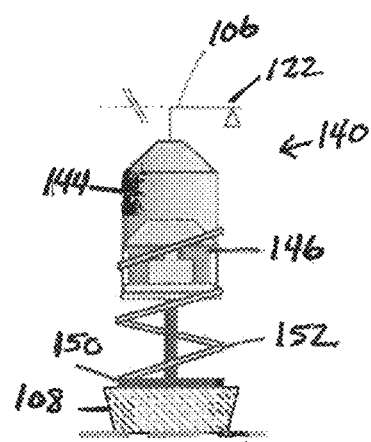

FIG. 4C shows the disposable piston pump assembly 140 configuration at the completion of the retraction or refill stroke. The plunger 146 is fully retracted. The disposable piston pump assembly is primed, where the spring cap 150 and the plunger 146 have moved to a stop position and the reusable movable stage has returned to a hard stop position. The reusable inlet valve is open but there is no flow into the pump chamber due to pressure equalization between the pump chamber and the external fluid source. One-way outlet valves V1 114 and V2 118 are closed. The reusable mechanical actuator 110 (not shown) which drives the reusable movable stage is disengaged.

Figure 4D:
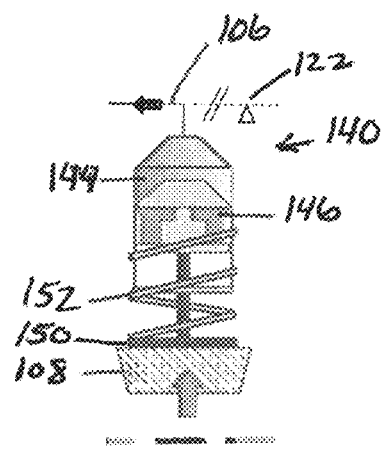

FIG. 4D shows an arrangement at a mid-point of the forward or pump stroke. The force for the forward stroke comes from activating the reusable movable stage 108. During the forward stroke, the reusable mechanical actuator 110 is engaged, moving the reusable movable stage 108 in the forward direction. At the same time, contact is made against the spring cap 150, and the forward motion of the reusable movable stage 108 pushes against the spring cap 150, moving the plunger 146 forward. Forward motion of the reusable movable stage also acts on the spring cap 150 to cause compression of the spring 152. Activation of the forward stroke coincides with mechanical action to close the reusable inlet valve. The increased pressure in the pump chamber during the forward stroke causes fluid to exit the pump chamber under pressure (greater than atmospheric). The increased pressure of the fluid causes one-way outlet valves V1 114 and V2 118 (not shown) from closed positions to open positions. During the pump stroke, the reusable component 102 has a dual energy transfer function. Mechanical force exerted by the reusable movable stage 108 is transferred to the disposable component 101 to move the plunger 146 and increase fluid pressure. Also, mechanical force exerted by the reusable movable stage 108 is transferred to the disposable component 101 to compress the spring 152, which stores mechanical energy until the refill stroke.

Figure 4E:
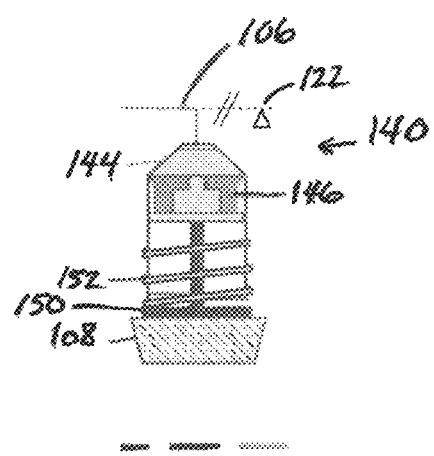

At the completion of the forward stroke the plunger 146 is in the forward position. The pump chamber 144 is substantially empty of fluid. The spring 152 is compressed from its resting position. Mechanical energy is stored in the spring 152. This situation is as depicted in FIG. 4E, which duplicates FIG. 4A. The sequence depicted in FIGS. 4A-4E repeats itself until the desired volume of fluid is infused. The sequence is driven at a frequency corresponding to the desired rate set by the user.

To summarize, mechanical energy transfer events needed to achieve the pumping actions of the disposable piston pump assembly 140 are shared between the reusable and disposable components, 102 and 101, respectively. During the pump stroke, forward motion of the reusable mechanical actuator 110 transfers energy to the disposable component 101 to move the plunger 146 and compress the spring 152. Mechanical energy stored by the disposable component 101 is released during the retraction stroke, to retract the plunger 146 and reposition the reusable movable stage 108.

Figure 5A:
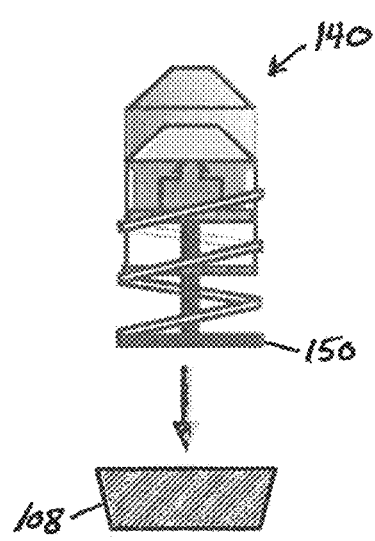
FIGS. 5A, 5B, and 5C show the relative positions of the disposable pump assembly and the reusable movable stage during connection of the disposable component and the reusable component, when the disposable component and the reusable component are attached, and during detachment of the disposable component and the reusable component, respectively.
Figure 5B:
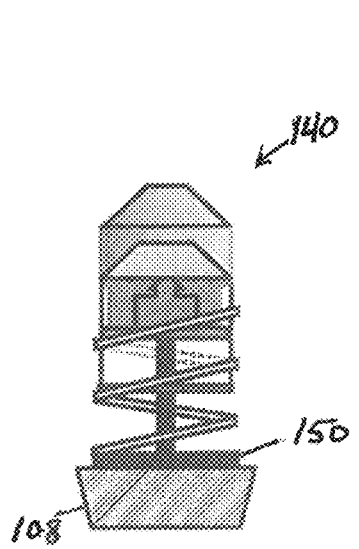
Figure 5C:
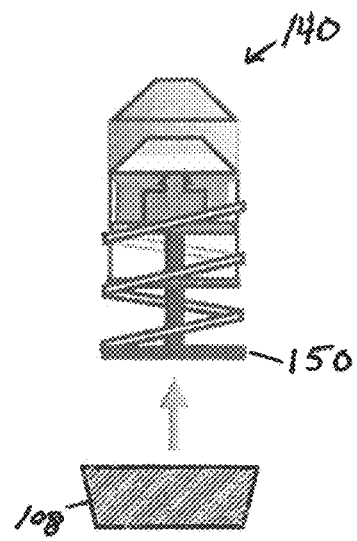

The disposable piston pump assembly 140 operates entirely without attachment mechanism or linking device between the reusable movable stage 108 and the spring cap 150 of the disposable piston pump assembly 140. Movement in the forward direction is achieved by applying a force from the reusable component 102 via a contact surface only. Similarly, movement in the retraction direction is achieved by applying a force from the disposable component 101 via contact surfaces only. As shown in FIGS. 5A, 5B, and 5C, this arrangement allows easy and rapid insertion of the disposable component 101, since there is no mechanical connection or disconnection step required to couple together the spring cap 150 and the reusable movable stage 108. FIG. 5A shows the disposable piston pump assembly 140 being brought into contact with the reusable movable stage 108 as the disposable component 101 (not shown) is attached to the reusable component 102 (not shown). FIG. 5B shows the disposable piston pump assembly 140 in contact with the reusable movable stage 108 when the disposable component 101 (not shown) and the reusable component 102 (not shown) are attached together. FIG. 5C shows the disposable piston pump assembly 140 being removed from contact with the reusable movable stage 108 as the disposable component 101 (not shown) is detached from the reusable component 102 (not shown).

Figures 6A, 6B:
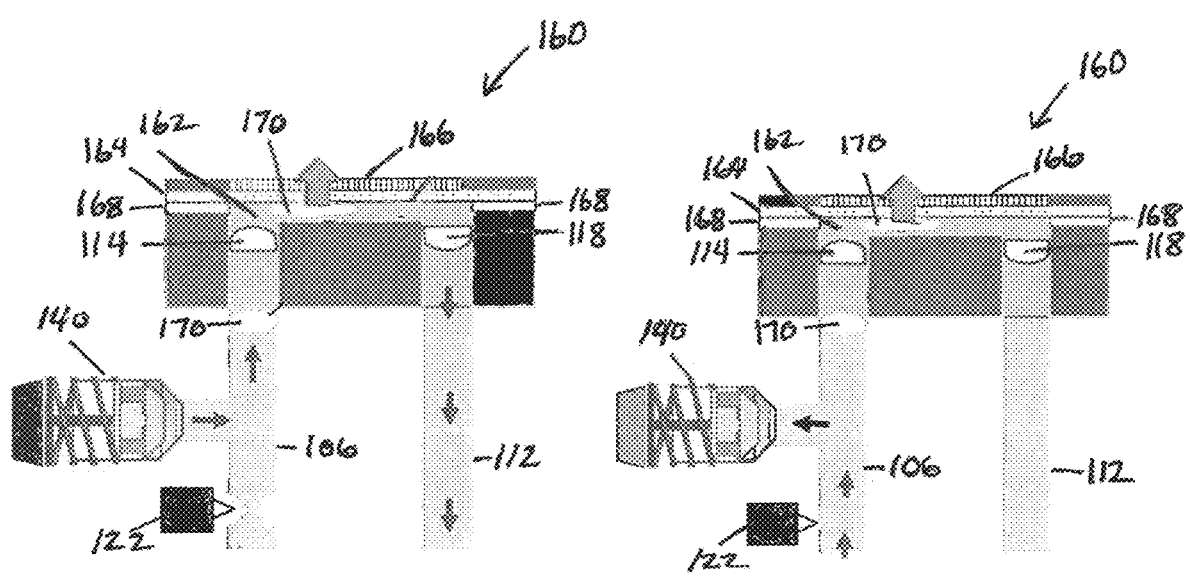
FIGS. 6A and 6B show the disposable bubble eliminator during the pump stroke of the disposable pump assembly and during the refill stroke of the disposable pump assembly, respectively.

Disposable Bubble Eliminator. FIGS. 6A and 6B show the disposable bubble eliminator 160 during the pump stroke of the disposable piston pump assembly 140 and during the refill stroke of the disposable piston pump assembly 140, respectively. FIGS. 6A and 6B show the disposable bubble eliminator 160, which includes a bubble eliminator chamber 162 in fluid communication with the first disposable conduit 106 and the second disposable conduit 112; a porous membrane 164 disposed as a wall of the bubble eliminator chamber 162 and in fluid communication with the atmosphere; and a mesh backing 166 disposed on an exterior surface of the porous membrane 164. The disposable bubble eliminator 160 may also include one or more flow spacers 168.

The disposable bubble eliminator 160 is used to prevent or minimize the risk of injury to the patient from air embolism during delivery of fluids to the body. Dissolved gasses within the delivered fluid can form bubbles out of solution due to pressure changes, temperature changes, flow irregularities, or other factors. A need exists for a device that removes gas bubbles and/or dissolved gas from fluids delivered to a patient via the intravenous route during a medical procedure. A need also exists for such a device that can be located at a point in the fluid delivery line near the patient, to minimize the potential for bubble formation between the device and the patient. The present invention includes a gas elimination device meeting these and other needs. The disposable bubble eliminator 160 uses the porous membrane 164 in contact with a fluid. Gas passes from the fluid and into the surrounding atmosphere due to a pressure differential. The disposable bubble eliminator 160, with associated one-way valves V1 114 and V2 118 (shown in FIGS. 6A and 6B), is designed to match the mechanics of the disposable piston pump assembly 140 and achieves coordination with the action of the disposable piston pump assembly 140 in a specific way. The disposable bubble eliminator 160 of an embodiment of the present invention is capable of exactly managing the pressure of the fluid present inside the bubble eliminator chamber 162 as the disposable piston pump assembly 140 alternates between forward and priming strokes. Management of the pressure of the fluid within the bubble eliminator chamber 162 is essential for proper function of the disposable bubble eliminator 160 and avoids disposable piston pump assembly 140 failure.

Coordinated Action with the Disposable Piston Pump Assembly 140. FIGS. 6A and 6B show the disposable bubble eliminator 160 arrangement with depiction of the fluid flow path during the forward and prime stokes of the disposable piston pump assembly 140. The disposable bubble eliminator 160 shown includes the bubble eliminator chamber 162 with dimensions of 0.85 in×1.0 in×0.004 in and an internal volume of 0.0034 in$^3$. The porous membrane 164, which may include expanded polytetraflouroethylene (ePTFE), forms a portion of side wall of the bubble eliminator chamber 162. The air permeability of the porous membrane 164 can be 0.20-0.45 ft$^3$/min/ft$^2$. The purpose of the porous membrane 164 is to allow gas to permeate through the filter via a positive pressure differential between the two sides of the porous membrane 164. A mesh backing 166 provides mechanical support to the porous membrane 164. The flow spacers 168 form a mechanical gas-tight seal.

Representative bubbles 170 are also shown. The disposable bubble eliminator 160 is positioned in the fluid flow path between one-way outlet valves V1 114 and V2 118. One-way outlet valve V1 114 is located at the fluid entry side of the bubble eliminator chamber 162. One-way outlet valve V1 114 is a silicone umbrella-type valve allowing flow in one direction and checks flow in the opposite direction. One-way outlet valve V1 114 is engineered to open under a specific cracking pressure of 0.03 psig (Minivalve UM 070.004). The one-way outlet valve V2 118 is located at the fluid exit side of the bubble eliminator chamber 162. The one-way outlet valve V2 118 is an umbrella type with a cracking pressure of 2.4 psig (Minivalve UM 070.006). The one-way outlet valves V1 114 and V2 118 are passive: they are not controlled electrically. FIG. 6A shows the disposable bubble eliminator 160 during the forward stroke of the disposable piston pump assembly 140, when the reusable inlet valve 122 is closed and the pump chamber 144 is being pressurized by the forward motion of the plunger 146. During the forward stoke, pressure in the fluid flow path between the reusable inlet valve 122 and one-way outlet valve V1 114 reaches values of 7-9 psig (pounds per square inch gauge). Gauge pressure is a measure of the fluid pressure relative to ambient atmospheric pressure. Fluid flow is towards the disposable component outlet port 180. A decrease in fluid pressure occurs across valve one-way outlet valve V1 114, resulting in a fluid pressure of 5-7 psig inside the bubble eliminator chamber 162 and in the region of the porous membrane 164. Thus, there is a positive pressure differential between the bubble eliminator chamber 162 internal fluid and the external vent area, causing venting of gas from solution to the outside through the porous membrane 164. During the forward stroke, another pressure drop occurs across one-way outlet valve V2 118, such that the fluid pressure in the conduit between one-way outlet valve V2 118 and the disposable component outlet port 180 is 3.5-4.5 psig. One-way outlet valve V2 118, in the open position, contributes to the positive pressure of the fluid in the bubble eliminator chamber 162 versus the external vent area, causing venting of gas from the bubble eliminator chamber 162 to the outside through the porous membrane 164. The result is that during the forward stroke of the disposable piston pump assembly 140, bubbles are substantially eliminated from the fluid occupying the bubble eliminator chamber 162.

FIG. 6B represents the fluid flow path during the prime stoke, during withdrawal of the plunger 146 and when reusable inlet valve 122 opens. The action of the plunger 146 causes depressurization of the fluid flow path, such that fluid is drawn in from an external fluid source via reusable inlet valve 122. Fluid pressure in the vicinity of the piston pump chamber 144 may be at −2.5 psig below the ambient atmospheric pressure. Depressurization of the fluid flow path causes the one-way outlet valves V1 114 and V2 118 (not shown) to close. Closure of one-way outlet valves V1 114 and V2 118 during the prime stroke is vital for correct function of the disposable bubble eliminator 160 and for correct function of the overall pump 100. Because one-way valve V1 114 is located at the fluid entry side of the bubble eliminator chamber 162, it mechanically and hydraulically isolates the fluid in the bubble eliminator chamber 162 from fluid depressurization caused by the withdrawal action of the plunger 146. Thereby depressurization of the disposable bubble elimination chamber 162 is substantially avoided when one-way valve V1 114 closes. Consider if one-way valve V1 114 was not present at or near the bubble eliminator chamber 162 fluid entry point. Without isolation of the bubble eliminator chamber 162 from the disposable piston pump assembly 140, depressurization of the bubble eliminator chamber 162 fluid would occur during the prime stroke. In that case, the fluid pressure within the bubble eliminator chamber 162 might equalize to the pressure of the surrounding atmosphere at the vent side of the porous membrane 164 and might fall below the pressure of the surrounding atmosphere at the vent side of the porous membrane 164. These situations favor air being drawn into the disposable bubble elimination chamber 162 from the outside via the porous membrane 164. This is undesirable. Excess air in the fluid flow path would compromise the ability of pump 100 to achieve fluid delivery to the patient in a controlled way. Fluid backflow towards the disposable component inlet port 104 would also occur, which is not desired. With continued cycling of the pump 100, there would be opportunity for gas bubbles to flow in the direction of the patient. Further, if this were to occur, the reusable bubble detector 126 located between one-way valve V2 118 and the patient side outlet 180 would be triggered, causing the pump to go into a patient-safe mode of operation.

One-way outlet valve V2 118 is located in communication with the fluid exit side of the bubble eliminator chamber 162. When it closes during the prime stroke of the disposable piston pump assembly 140, it mechanically and hydraulically isolates the fluid in the bubble eliminator chamber 162 from patient side disposable component outlet port 180. Depressurization of the fluid present in the disposable bubble eliminator 160 is thus minimized or prevented. The fluid pressure internal to the bubble eliminator chamber 162 is maintained at or close to 2.4 psig, as in FIG. 6B. Thus, during the prime stroke, the pressure differential across the porous membrane 164 is sufficient to cause venting of gas from solution to the outside atmosphere. The one-way outlet valve V2 118 plays an important role in managing the phenomenon of free flow. Free flow can occur when the vertical height of the disposable bubble eliminator 160 lies above the vertical height of the tubing or conduit connecting to the patient, such that gravity-driven flow of fluid in the direction of the patient outlet may occur. In the absence of the one-way outlet valve V2 118, free flow would cause fluid pressure in the bubble eliminator chamber 162 to decrease leading to siphoning of air into the bubble eliminator chamber 162 via the porous membrane 164. Having the one-way outlet valve V2 118 in the closed position minimizes this phenomenon. The presence of air intake into the bubble eliminator chamber 162 is undesirable. Excess air in the fluid flow path would compromise the ability of the pump 100 to achieve fluid flow and delivery to the patient in a controlled way. There would be opportunity for gas bubbles to flow in the direction of the patient. Further, if this occurred the reusable bubble detector 126 located between the one-way outlet valve V2 118 and the patient side outlet would be triggered, causing the pump to go into a patient-safe mode of operation.

The one-way outlet valves V1 114 and V2 118 (not shown) have dual function. Under pressure during the forward disposable piston pump assembly 140 stroke, the one-way outlet valves V1 114 and V2118 open, but because of their orientation they only allow fluid to pass in the direction of the patient outlet. As the fluid tries to reverse direction, the one-way outlet valves V1 114 and V2 118, being umbrella valves, close and prevent any fluid from traveling towards the fluid inlet.

Disposable Bubble Eliminator 160 Design Details. The disposable bubble eliminator 160 incorporates a low-cost air permeable, porous membrane 164 that is capable of venting bubbles from the fluid as it is pumped. Expanded Polytetraflouroethylene (ePTFE) is commonly used in fluid separation applications in medical devices due to its biocompatibility and ability to resist wetting out. Air is allowed to permeate through the filter via a positive pressure differential between the two sides of the porous membrane 164. This means that the fluid side must always remain at a higher pressure than the atmosphere, otherwise it is possible to pull air into the fluid stream from outside the disposable bubble eliminator 160. Therefore, the vent needs to be strategically placed in the flow such that positive pressure conditions can be maintained at all times. By placing the ePTFE vent on the patient side of the disposable piston pump assembly 140, the fluid pressure is maintained to be at least atmospheric throughout operation. One-way outlet valve V1 114 (not shown) prevents the prime stroke from pulling a vacuum on the vent downstream, also known as backflow. The one-way outlet valve V2 118 (not shown), with a suitably high cracking pressure, ensures that no air is pulled into the line by syphoning when the needle is below the disposable bubble eliminator 160. The latter scenario is known as free-flow.

Expanded PTFE membranes come in many different blends that vary in air permeability rates (ft³/min/ft²), thickness, pore size (μm), burst pressure, and hydrophobicity. Increased air permeability is an obvious advantage for bubble elimination at high flow rates, but it typically comes at the expense of burst pressure. A sufficiently breathable membrane must also allow several factors of safety for nominal and off-nominal pressure scenarios. As fluid pressure increases, it is typical for the membrane to deform outward into a dome shape. This not only poses a strength-of-materials risk but changes the venting criteria vital to effective air removal, as discussed herein. To mitigate this, a rigid mesh backing 166 is secured on the outside of the ePTFE membrane, which permits air breathability while maintaining the flat shape desired for venting.

Several factors determine the efficacy of the porous membrane 164 during pumping: bubble length, travel time, velocity, and pressure difference. To start, the pump 100 has a large range of flow rates at which it must facilitate this safety feature of removing gas from the fluid. These flow rates are accentuated by the duty cycle of the priming and pumping strokes: at an average flow rate of 500 mL/hr, the instantaneous flow rate in the fluid may be closer to 1,000 mL/hr. This translates to a very brief time that a fluid particle has in contact with the porous membrane 164, called residence time. The air bubble must have a sufficient residence time to allow mass transport to occur. Mass transport is the movement of air molecules through the pores of the porous membrane 164 caused by the pressure differential across the ePTFE. There is an inherent time required to pass a given number of molecules through the porous membrane 164, a value dictated by the material permeability and fluid pressure. It is desirable to maximize the bubble's exposure on the porous membrane 164 to allow all air molecules enough time to escape. Residence time can be controlled by slowing the velocity of the fluid through deliberate geometric design of the flow path: when increasing the travel length l for a given velocity, the residence must increase. Additionally, by expanding the fluid cross-sectional area to a critical dimension (thickness and width A), the velocity may be reduced to an effective value relative to other geometries for a given flow rate $\dot{m}$ as understood by Equation 1:

$$v = \frac{l}{t} = \frac{\dot{m}}{A}$$

A liquid-gas interface creates a contact angle between the porous membrane 164 and the bubble boundary. As the bubble velocity increases, this contact angle approaches zero for which no triple point (air, membrane, liquid) exists and a stable film is formed. The film inhibits the direct exposure of air molecules to the porous membrane 164. The bubble velocity then must be less than a critical value at which the film forms to prevent any mass transfer from occurring. This critical velocity is governed by Equation 2:

$$v_c = \frac{1}{9\sqrt{3}} \frac{\gamma/\mu}{20} \theta_E^3$$

In Equation 1, γ is the surface tension between gas and liquid, μ is the viscosity of the gas, and $\theta_E$ is the contact angle of the bubble on the porous membrane 164 surface.

Regarding cross-sectional area, there is an optimal value to which porous membrane 164 performance and pump 100 capability must be found. It is favorable to spread the bubble as wide and thin as possible so as to expose a greater area of air to the porous membrane 164 and thus vent in a shorter amount of time. One obvious limitation is disposable bubble eliminator 160 space. However, perhaps more important is the effect of pressure losses through the disposable bubble eliminator chamber 162. A variation in flow field thickness impacts the pressure by a power of two. Increased pressure during the infusion stroke translates to a higher effective power required by the pump actuation mechanisms. Thus, an improperly designed bubble vent will cost the system valuable battery life to perform its normal function, or otherwise not effectively disperse a bubble to an area conducive for complete mass transport. The disposable bubble eliminator 160 design presented by the present invention provides a unique solution to the problems identified above.

The design of the disposable bubble eliminator 160 was iterated many times before reaching a suitable configuration for all fluid types. Initial proof of concept designs, which showed effective bubble removal in water, had to be greatly re-evaluated once testing with whole blood and blood component samples such as packed red blood cells. The complex multi-component makeup, along with altered fluid characteristics, meant that bubbles could not effectively be removed even at low flow rates. Additionally, blood cell damage (hemolysis) must be considered when designing the disposable bubble eliminator 160. Methods that cause extreme shear stress or have excessively rough surface finishes could cause patient harm, so careful testing and analysis must be performed when designing this feature.

The functioning design must minimize the velocity of the fluid across the membrane, thus increasing its residence time to vent all air. Velocity is a function of flow rate and the cross-sectional area of the flow field: increasing the area decreases the velocity at a given flow rate. However, the width will be limited by the overall size requirements of the disposable bubble eliminator 160 and the thickness will be limited by pressure drop as the fluid tries to pass through it. The path length may also be varied to increase residence time but must also consider size and pressure constraints. A membrane exhibiting superior air permeability rates could reduce the overall size required to vent the bubble, but its pore size, burst pressure, and biocompatibility will determine if its selection is appropriate in this application.

The general design parameters of the disposable bubble eliminator 160 are shown in Table 1. These outline the variables that are combined to make for an effective disposable bubble eliminator 160. The table serves as a non-limiting example for a functional embodiment of a disposable bubble eliminator 160 as it is used with the pump 100.

TABLE 1 of Variables for Disposable Bubble Eliminator 160

| # | Variable | Range | Requirements |
|---|---|---|---|
| 1 | Flow Rate | 0.1-999 mL/hr | System Requirement Threshold |
| 2 | Bubble Volume | 50-100 uL | System Requirement Threshold |
| 3 | Compact Size | 0.005-0.15 in$^3$ | System Requirement Threshold |
| 4 | Pressure | 0.1-10 PSIG | Atmospheric < P < Burst Pressure |
| 5 | Membrane Air Permeability | 0.20-0.45 ft$^3$/min/ft$^2$ @ 125 Pa | Permeability should not drastically minimize burst pressure rating |
| 6 | Path Length | 0.6-0.7 in | L >> H |
| 7 | Path Width | 0.85-1.0 in | Maximize bubble area |
| 8 | Flow Field Thickness | 0.004-0.007 in | Pressure drop should not be excessive |
| 9 | Velocity | 5-15 in/s | $V < V_{Critical}$ |
| 10 | Residence Time | 0.06-0.17 s | $T_{Residence}$ < Time required to vent all air |

To reach a suitable design of the disposable bubble eliminator 160, a specific set of tests were conducted which introduced regulated bubbles into a controlled stream of fluid, which was directed to flow to the bubble eliminator chamber test subject (with dimensions varied as indicated below). A syringe pump was used to control the rate of liquid flow. A 3 mL syringe was connected by an in-line three-way luer-lock valve upstream of the test subject. At the time of test, the valve was opened to allow a 0.2-1.0 mL air bubble into the free stream from the syringe. A 7 mL syringe downstream of the test piece collected all liquid and air pumped through the bubble eliminator chamber 162, and the remaining air bubble was measured and compared against the input volume. Each disposable bubble eliminator 160 design iteration was recorded to pass or fail based on its ability to remove over 50% of air from fluid at all three distinct flow rates: 50 mL/hr, 1,000 mL/hr, and 2,000 mL/hr.

Figures 7C, 7D, 7E:
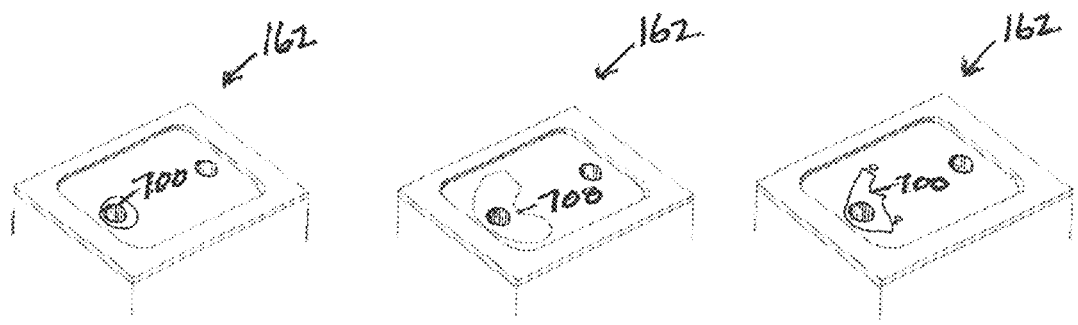
FIGS. 7C-7G show the disposable bubble eliminator effectively performing, with a bubble progressively becoming smaller as the bubble's air passes out through the ePTFE membrane.

FIGS. 7A-7G depict the bubble eliminator chamber 162 in one embodiment. In FIG. 7A, length l is defined by the distance from the center points of the inlet and outlet. Width w is defined by the distance from either wall perpendicular to the mean flow direction. Thickness t is defined by the spacer 168 height as shown. It is assumed that the porous membrane 164 (not sown) exists on the top plane of the depicted bubble eliminator chamber 162, forming a hydraulic seal around the rectangular housing. The fluid inlet is the left-hand cylindrical borehole which is perpendicular to the plane of the bubble eliminator chamber 162. The fluid outlet is the right-hand cylindrical borehole which is perpendicular to the plane of the bubble eliminator chamber 162. FIG. 7B depicts the approximate flow lines for this embodiment by arrows. A large distribution of flow passes through the direct line between the inlet and outlet, while slower flow is pushed toward the periphery of the bubble eliminator chamber 162. Computational fluid dynamic analysis shows that the highest pressure exists nearest the inlet port and gradually decreases as flow moves to the outlet port.

FIG. 7C depicts a bubble 700 of approximately 500 uL in volume beginning to enter the bubble eliminator chamber 162 through the inlet port. The fluid is flowing at the highest expected flow rate of 2,000 mL/hr as controlled by a syringe pump. Not all of the bubble has entered the bubble eliminator chamber 162. A relatively circular distribution of the bubble begins to form on the surface of the ePTFE.

FIG. 7D depicts the bubble 700 of approximately 500 uL in volume continuing to fill the bubble eliminator chamber 162. It expands in area as it enters the bubble eliminator chamber 162, but it may or may not take the shape depicted in FIG. 7D; the shape shown is exemplary and non-limiting.

A significant portion of the air within the bubble is in direct contact with the ePTFE membrane and is vented with a rate defined by the air permeability and instantaneous local pressure in the bubble eliminator chamber 162. No stable film exists between the bubble and the membrane due to the velocity with which the bubble moves across the membrane.

FIG. 7E depicts the bubble 700 beginning to lose volume within the bubble eliminator chamber 162. As it does so, the leading edges of the bubble reverse in on itself while more air continues to enter form the inlet port. It is common for smaller bubbles (less than 50 μL) to form as the parent bubble collapses, however it may or may not take the shape depicted in FIG. 7E; the shape shown is exemplary and non-limiting.

Figure 7F:
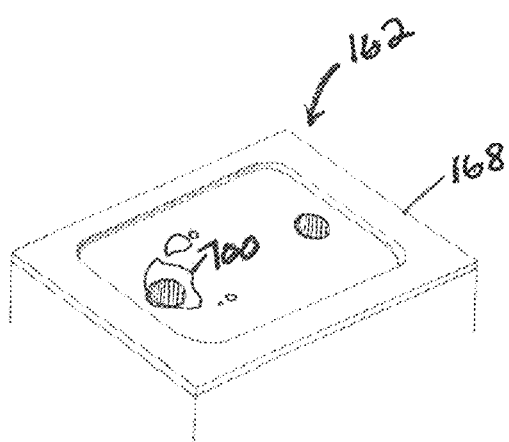

FIG. 7F depicts the bubble 700 continuing to lose volume within the bubble eliminator chamber 162. Smaller bubbles have broken off from the original bubble but continue to vent.

Figure 7G:
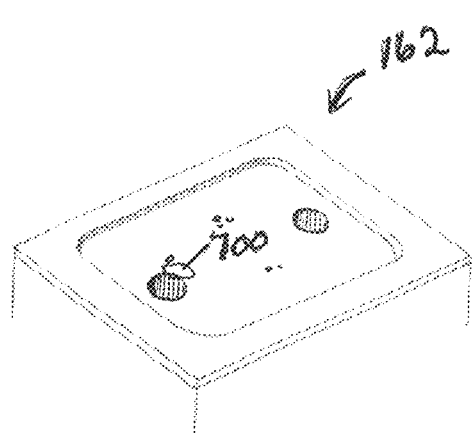

FIG. 7G depicts the last remaining air bubbles of bubble 700 within the bubble eliminator chamber 162. At this point, the air in the fluid flow is significantly reduced in volume. Bubbles of very small size (less than 20 μL) commonly move through the remainder of the bubble eliminator chamber 162 without being eliminated. This is due to the ratio of bubble volume to its dispersed area and the contact angle formed with a more spherical bubble as opposed to a flattened bubble.

FIGS. 7C-7G depict the disposable bubble eliminator 160 effectively performing in one embodiment, with the bubble progressively becoming smaller as the bubble's air passes out through the porous membrane 164 (not shown). The test case shown here would be considered a passing criterion as it properly removed >50% of a bubble of 500 μL in volume from a fluid passing at 2,000 mL/hr. The fluid flow path sufficiently controlled the bubble to a velocity in which no stable film formed between the air boundary and the porous membrane 164. The fluid flow path sufficiently dispersed the bubble to an area conducive to vent the air quickly. The fluid flow path was long enough to allow the elimination of the air before it escaped the bubble eliminator chamber 162. The chosen porous membrane 164 sufficiently passed air across itself under the given pressure without harm or risk of bursting.

FIGS. 8A-8K and Table 2 illustrate results of a study to investigate various bubble venting specifications, Examples 1-11. FIGS. 8A-8K each depict top views and side views of the bubble eliminator chamber 162 and bubble 800. Porous membrane 164 is also shown.

TABLE 2

Results of a study to investigate various bubble venting specifications for Examples 1-11.

Figures 8A, 8B:
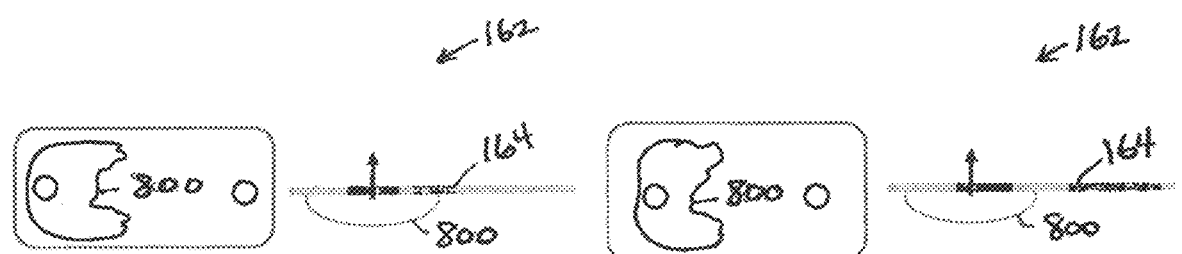
FIGS. 8A-8K show results of a study to investigate various bubble venting specifications, Examples 1-11.
Figures 8C, 8D:
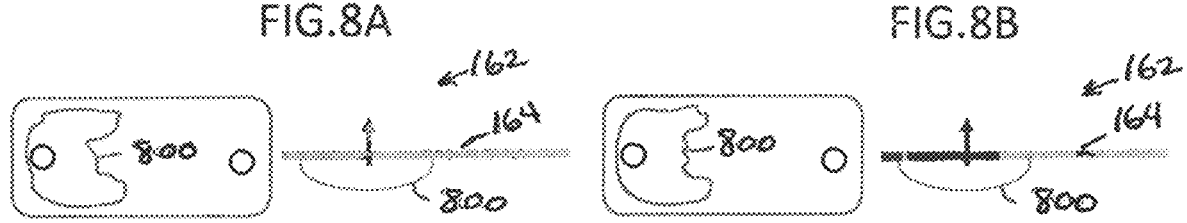
Figure 8E:
Figure 8F:
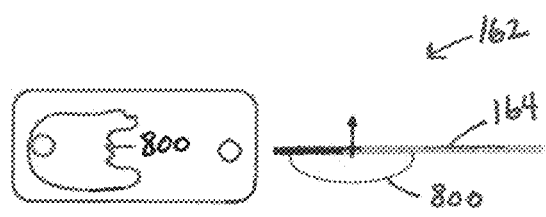
Figure 8G:
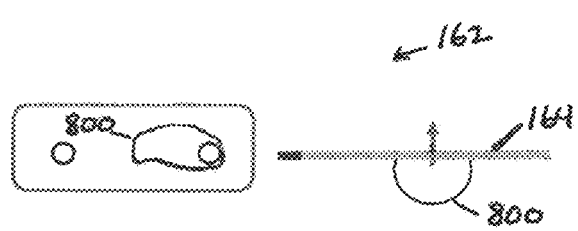
Figure 8H:
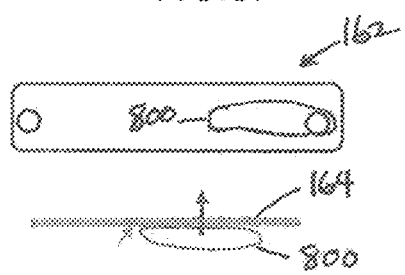
Figure 8I:
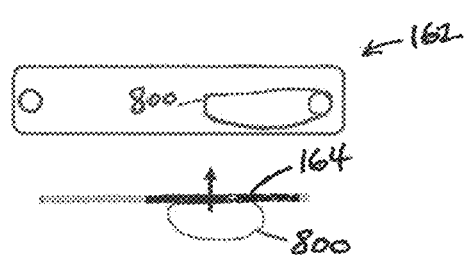
Figure 8J:
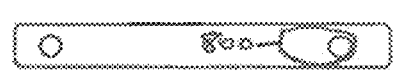
Figure 8K:
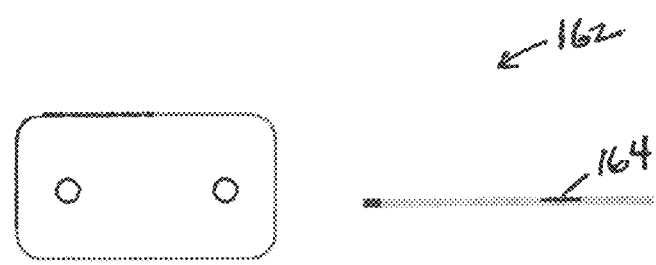

| Figure | Example | Design | Observation | Pass/Fail |
|---|---|---|---|---|
| FIG. 8A | 1 (blood) | Pathlength 0.6 in<br>Path width 0.85 in<br>Flow Field thickness 0.004 in<br>Velocity 9.9 in/sec<br>Residence time 0.6 sec | No failures: bubble removed >90% | Pass |
| FIG. 8B | 2 (blood) | Path length 0.5 in<br>Path width 1.0 in<br>Flow Field thickness 0.004 in<br>Velocity 8.4 in/sec<br>Residence time 0.6 sec | No failures: bubble removed >90% | Pass |
| FIG. 8C | 3 (blood) | Pathlength 0.6 in<br>Path width 0.85 in<br>Flow Field thickness 0.008 in<br>Velocity 4.9 in/sec<br>Residence time 0.12 sec | No failures: bubble removed >90% | Pass |
| FIG. 8D | 4 (saline) | Path length 0.6 in<br>Path width 0.85 in<br>Flow Field thickness 0.004 in<br>Velocity 9.9 in/sec<br>Residence time 0.06 sec | No failures: bubble removed >90% | Pass |
| FIG. 8E | 5 (saline) | Path length 0.6 in<br>Path width 0.85 in<br>Flow Field thickness 0.008 in<br>Velocity 4.9 in/sec<br>Residence time 0.12 sec | No failures: bubble removed >90% | Pass |
| FIG. 8F | 6 (saline) | Path length 0.6 in<br>Path width 0.85 in<br>Flow Field thickness 0.008 in<br>Velocity 4.9 in/sec<br>Residence time 0.12 sec | No failures: bubble removed >90% | Pass |
| FIG. 8G | 7 (blood) | Path length 0.5 in<br>Path width 0.5 in<br>Flow Field thickness 0.004 in<br>Velocity 16.9 in/sec<br>Residence time 0.03 sec | Bubble breakthrough: insufficient contact area and residence time | Fail |
| FIG. 8H | 8 (blood) | Path length 1.0 in<br>Path width 0.42 in<br>Flow Field thickness 0.004 in<br>Velocity 19.7 in/sec<br>Residence time 0.03 sec | Bubble breakthrough: insufficient contact area and residence time | Fail |
| FIG. 8I | 9 (blood) | Path length 1.0 in<br>Path width 0.42 in<br>Flow Field thickness 0.008 in<br>Velocity 9.8 in/sec<br>Residence time 0.06 sec | Bubble breakthrough: insufficient contact area and residence time | Fail |
| FIG. 8J | 10 (blood) | Path length 1.2 in<br>Path width 0.25 in<br>Flow Field thickness 0.05 in<br>Velocity 2.7 in/sec<br>Residence time 0.44 sec | Bubble breakthrough: insufficient contact area and residence time | Fail |
| FIG. 8K | 11 (blood) | Pathlength 0.6 in<br>Path width 1.5 in<br>Flow Field thickness 0.002 in<br>Velocity 11.1 in/sec<br>Residence time 0.05 sec | Excessive pressure drop; pump loses performance | Fail |

These values make assumptions about the fluid's viscosity, Reynolds number, and flow rate. In each example, the disposable piston pump assembly 140 specifications were: stroke volume=0.7 mL; piston chamber 144 ID 0.59 in; stroke length 0.156 in. The spring 152 of the disposable piston pump assembly 140 was of stainless steel (Century Spring): free length 1.16 in; compressed length 0.35 in; ID 0.695 in; stiffness 1.3 lb/in priming force 1-0.4 lb; infusing force 0.4-1.6 lb. The plunger 146 was a loss of resistance (LOR) lip seal type (Portex). The porous membrane 164 material was ePTFE (Sterlitech): thickness=0.008-0012 in. Repeated forward motion of the plunger 146 was achieved using an Admet mechanical actuator.

Examples 1 and 2 (FIGS. 8A and 8B, respectively) were conducted using blood. Bubble elimination was achieved successfully. These examples specify a successful design in terms of the disposable bubble eliminator chamber 162 dimensions relative to flow velocity, for adequate bubble contact with the porous membrane 164 leading to bubble elimination. Confinement of the bubble 800 in the bubble eliminator chamber 162 is important. The flow field thickness was 0.004 in. We observed that the ellipse of the bubble at the liquid membrane interface was highly oblate, indicative of a "flattened" bubble geometry, favorable to rapid gas exchange.

Example 3 (FIG. 8C) was less successful than Examples 1 and 2. The design was marginal. A lower velocity and longer residence time should benefit gas bubble venting but the expected benefit did not occur. We observed that the ellipse of the bubble 800 at the liquid membrane interface was more circular, less oblate, indicating the bubble 800 was less confined and closer to spherical geometry in the channel than in Examples 1 and 2. This design with its thicker flow field thickness (0.008 in vs 0.004 in) is less favorable to venting.

Examples 4-6 (FIGS. 8D-8F, respectively) involved substitution of blood for saline solution. The low viscous nature of Ringer's solution compared to blood improved the performance of the vent, resulting in three successful trials.

Example 7 (FIG. 8G) was an ineffective design when tested with blood. The high flow velocity and short residence time was detrimental to bubble elimination. We observed that the ellipse of the bubble 800 at the liquid membrane interface tended to be circular rather than oblate (flattened) limiting the amount of bubble surface area was in contact with the porous membrane 164. Therefore, despite possibly having no stable film developed between the air and the membrane, the bubble 800 did not have the time required to transfer air across the porous membrane 164.

Example 8 (FIG. 8H) was an ineffective design when tested with blood. The high flow velocity and short residence time was detrimental to bubble elimination. The velocity exceeded the critical value for which a stable film is formed between the air and the membrane. Despite the increased travel length, the film prevented the transfer of air across the permeable membrane, thus allowing all of the bubble 800 to escape the bubble eliminator chamber 162.

Example 9 (FIG. 8I) was an ineffective design when tested with blood. We observed that the ellipse of the bubble at the liquid membrane interface tended to be circular rather than oblate (flattened) which limited the amount of bubble surface area was in contact with the porous membrane 164. The flow path width was too narrow to effectively disperse the bubble for maximum contact with the porous membrane 164.

Example 10 (FIG. 8J) was an ineffective design due to its flow field thickness of 0.05 in. While the velocity was low enough to prevent the formation of a stable film between the air and membrane, the circular cross-section of the bubble resulted in a very low contact area to the membrane. Thus, air could not escape the bubble eliminator chamber 162.

Example 11 (FIG. 8K) was an ineffective design due to the excessive pressure drop experienced by the fluid. Despite the bubble being significantly dispersed and having sufficient velocity for mass transfer, the pressure losses due to the extremely narrow flow chamber put undue stress on the pump 100. Increased pressure drop in the bubble eliminator chamber 162 is undesirable because it translates to increased power consumption by the pump.

FIGS. 9A-9D schematically depict Examples 12-15, representing additional configurations tested. Each example shows the effect of modified valve configurations on the pump's function. In each example, the specifications of the disposable piston pump assembly 140 were: stroke volume=0.7 mL; piston chamber 144 ID 0.59 in; stroke length 0.156 in. The spring 152 was of stainless steel (Century Spring): free length 1.16 in; compressed length 0.35 in; ID 0.695 in; stiffness 1.3 lb/in priming force 1-0.4 lb; infusing force 0.4-1.6 lb. The plunger 146 was a loss of resistance (LOR) lip seal type (Portex). The porous membrane 164 material was ePTFE (Sterlitech): thickness=0.008-0.0012 in.

Figure 9A:
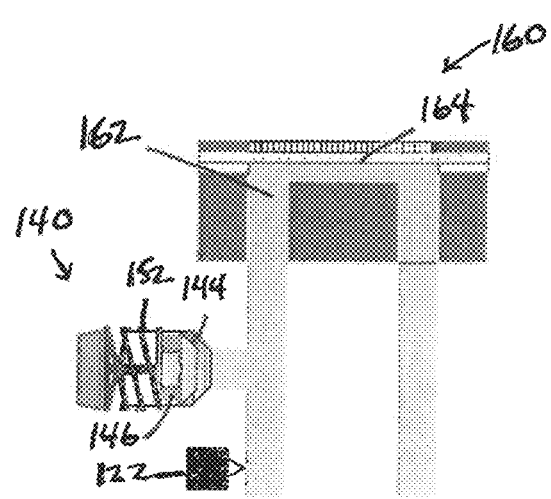
FIGS. 9A-9D schematically depict Examples 12-15, representing additional configurations tested.

Example 12 (FIG. 9A). This is a pump configuration omitting the one-way outlet valves V1 114 and V2 118 from the fluid flow path. A pump 100 of this design was set to operate at a flow rate of 500 mL per hour. The fluid was whole blood. During the priming stroke, when valve 122 was open, significant air intake into the fluid flow line occurred caused by depressurization of the bubble eliminator chamber 162. Back flow was observed. Pump 100 operation became ineffective after a few cycles.

Figure 9B:
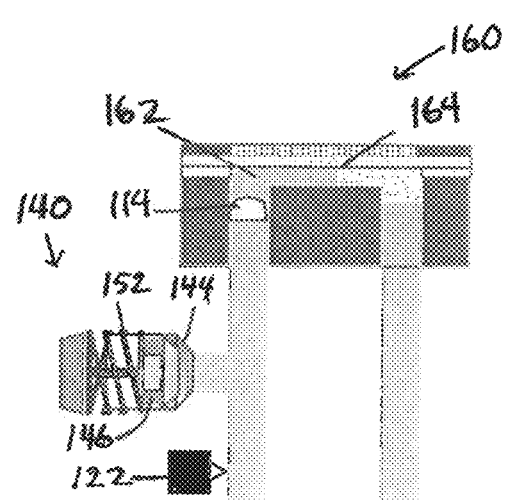

Example 13 (FIG. 9B). Fluid flow path includes one-way outlet valve V1 114 located at or near the bubble eliminator chamber 162 fluid entry point and is oriented to allow flow only in the direction of the disposable component outlet port 180 (not shown). There is no one-way outlet valve V2 118 in this configuration. The pump 100 was set to operate at 500 mL per hour flow rate using whole blood. Closure of one-way outlet valve V1 114 during disposable piston pump assembly 140 priming isolates the bubble eliminator chamber 162 from the depressurization effect due to retraction of the plunger 146. However, the bubble eliminator chamber 162 is not isolated from the patient disposable component outlet port 180 (not shown). Lower conduit height versus the height of the bubble eliminator chamber 162 caused fluid free flow in the direction of the disposable component outlet port 180. Concurrently, air siphoned into the bubble eliminator chamber 162 from the outside atmosphere via the gas permeable porous membrane 164. Pump 100 operation was ineffective after a few cycles due to excess air in the fluid flow path and inability to control the rate of fluid flow to the disposable component outlet port 180.

Figure 9C:
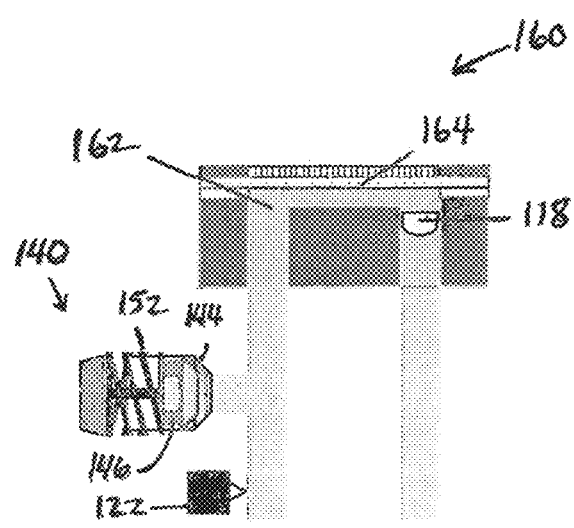

Example 14 (FIG. 9C). Fluid flow path includes the one-way outlet valve V2 118 in proximity to the fluid exit point of the disposable bubble eliminator 160, which is oriented to allow flow only in the direction of the disposable component outlet port 180 (not shown). There is no one-way outlet valve V1 114 in this example. The pump 100 was operated at 500 mL per hour flow rate using whole blood. Closure of the one-way outlet valve V2 118 during the disposable piston pump assembly 140 prime stroke isolated the bubble eliminator chamber 162 to prevent fluid free flow in the direction of the disposable component outlet port 180. However, the bubble eliminator chamber 162 is not isolated from the depressurization effect due to the retraction of the pump plunger 146. When the disposable piston pump assembly 140 was operated, air siphoned into the flow system across the gas permeable porous membrane 164 and fluid backflow was observed occurring from the bubble eliminator chamber 162 towards the disposable piston pump assembly 140. Pump 100 operation was ineffective after 10 cycles due to excess air in the fluid flow path and inability to control the rate of fluid flow to the disposable component outlet port 180.

Figure 9D:
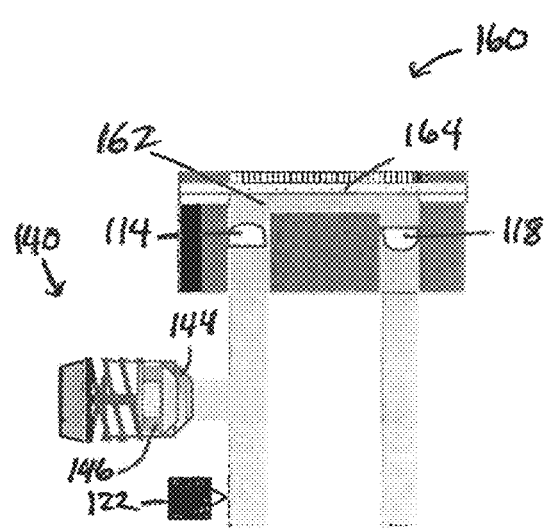

Example 15 (FIG. 9D). The fluid flow path includes one-way outlet valves V1 114 and V2 118 arranged and oriented as in FIGS. 1 and 2. The pump 100 was operated at 500 ml per hour using whole blood. Bubble elimination was effective. No air siphoned into the bubble eliminator chamber 162 even after extended use. The desired flow rate was constant at exactly at 500 mL/hr over hundreds of duty cycles of the pump.

Figure 10:
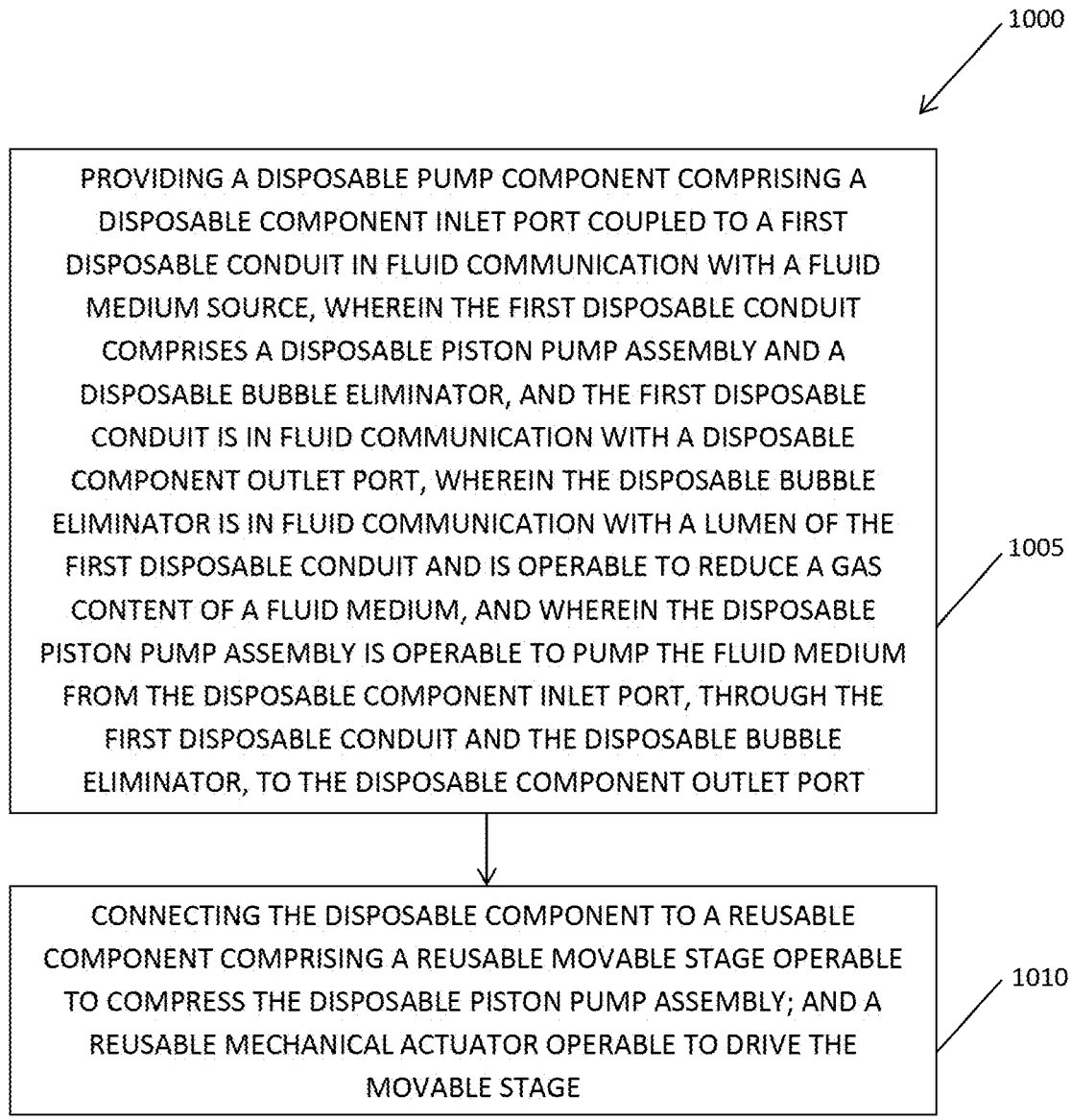
FIG. 10 shows a flowchart for a method embodiment of the present invention.

FIG. 10 shows a flowchart for a method embodiment of the present invention. Method 1000 includes in block 1005 providing a disposable pump component including a disposable component inlet port coupled to a first disposable conduit in fluid communication with a fluid medium source, wherein the first disposable conduit includes a disposable piston pump assembly and a disposable bubble eliminator, and the first disposable conduit is in fluid communication with a disposable component outlet port, wherein the disposable bubble eliminator is in fluid communication with a lumen of the first disposable conduit and is operable to reduce a gas content of a fluid medium, and wherein the disposable piston pump assembly is operable to pump the fluid medium from the disposable component inlet port, through the first disposable conduit and the disposable bubble eliminator, to the disposable component outlet port. Block 1010 includes connecting the disposable component to a reusable component including a reusable movable stage operable to compress the disposable piston pump assembly; and a reusable mechanical actuator operable to drive the movable stage.

Figure 11:
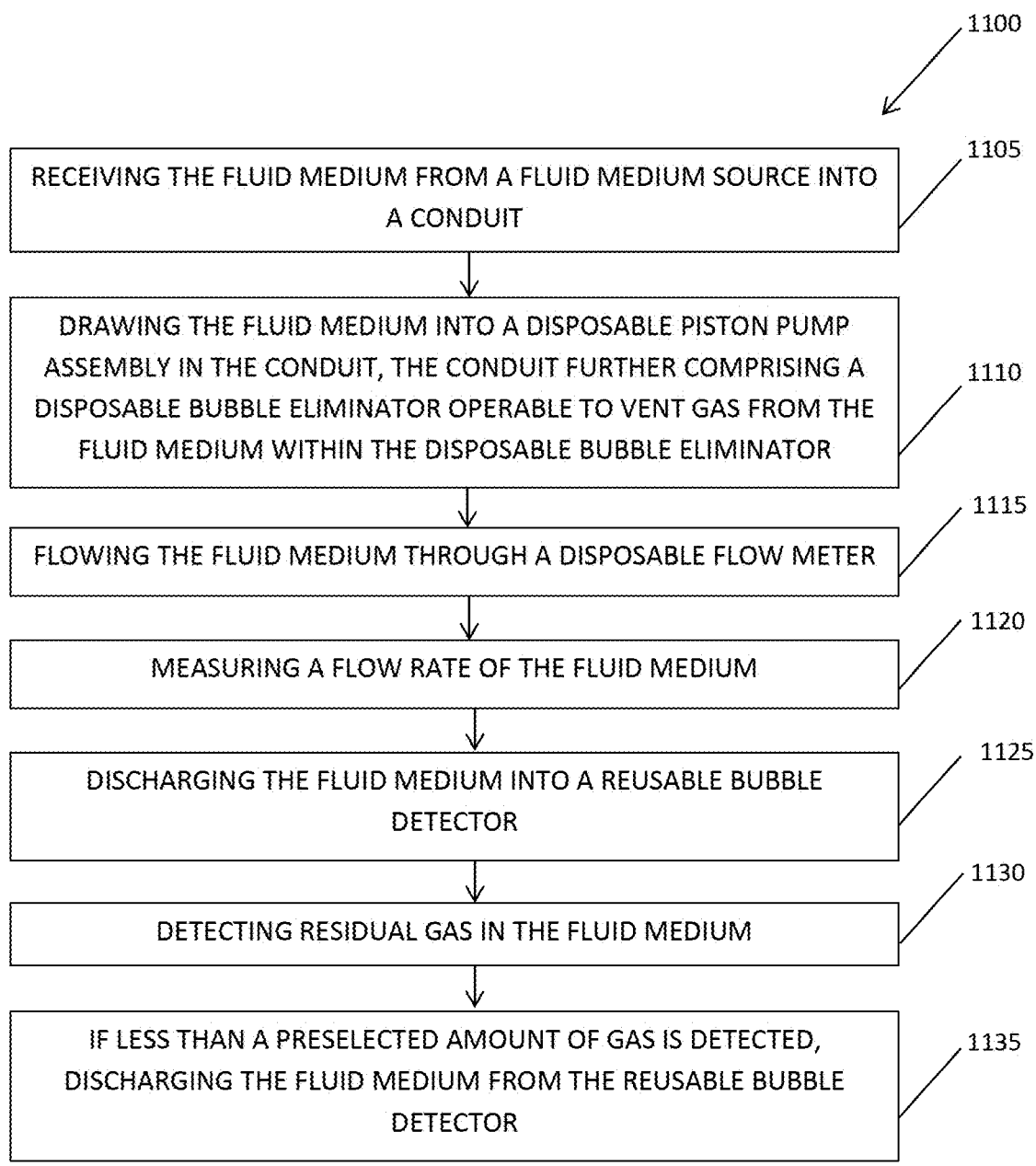
FIG. 11 shows a flowchart for another method embodiment of the present invention.

FIG. 11 shows a flowchart for another method embodiment of the present invention. Block 1105 of method 1100 of pumping a fluid medium includes receiving the fluid medium from a fluid medium source into a conduit. Block 1110 includes drawing the fluid medium into a disposable piston pump assembly in the conduit, the conduit further comprising a disposable bubble eliminator operable to vent gas from the fluid medium within the disposable bubble eliminator. Flowing the fluid medium through a disposable flow meter is included in block 1115. Measuring a flow rate of the fluid medium is included in block 1120. Block 1125 includes discharging the fluid medium into a reusable bubble detector. Block 1130 includes detecting residual gas in the fluid medium. Block 1135 includes discharging the fluid medium from the reusable bubble detector if less than a preselected amount of gas is detected.

The pump 100 may be included in a kit that also includes one or more other items commonly used when infusing liquids to a patient.

Those skilled in the art of infusion pumps will recognize that the pump 100, the methods 1000 and 1100 and the kit disclosed herein answer the need for an infusion pump that reduces or removes gases from fluids to be infused, is less costly than using and cleaning reusable pumps, ensures correct direction of fluid flow, prevents uncontrolled flow of fluid to be infused, and controls the rate of flow of fluid that is being infused.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of." As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step, or a limitation) or group of integers (e.g., feature(s), element(s), characteristic(s), property(ies), method/process(s) steps, or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about," "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the devices and/or methods disclosed and claimed herein can be made and executed without undue experimentation in light of the present disclosure. While the devices and/or methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope, and concept of the invention as defined by the appended claims.

Furthermore, no limitations are intended to the details of construction or design herein shown, other than as described in the claims below. It is therefore evident that the particular embodiments disclosed above may be altered or modified and all such variations are considered within the scope and spirit of the disclosure. Accordingly, the protection sought herein is as set forth in the claims below.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

To aid the Patent Office, and any readers of any patent issued on this application in interpreting the claims appended hereto, applicants wish to note that they do not intend any of the appended claims to invoke 35 U.S.C. § 112(f) as it exists on the date of filing hereof unless the words "means for" or "step for" are explicitly used in the particular claim.

What is claimed is:

1. A pump comprising:
a disposable component comprising:
a disposable component inlet port coupled to a first disposable conduit in fluid communication with a fluid medium source, wherein the first disposable conduit comprises a disposable piston pump assembly and a disposable bubble eliminator, and the first disposable conduit is in fluid communication with a disposable component outlet port, wherein the disposable bubble eliminator is in fluid communication with a lumen of the first disposable conduit and is operable to reduce a gas content of a fluid medium;
wherein the disposable piston pump assembly comprises a plunger in direct contact with the fluid medium, and wherein the disposable piston pump assembly is operable to pump the fluid medium from the disposable component inlet port, through the first disposable conduit and the disposable bubble eliminator, to the disposable component outlet port;
a first one-way outlet valve disposed in the first disposable conduit between the piston assembly and the disposable bubble eliminator and operable to prevent the fluid medium from flowing from the disposable bubble eliminator to the disposable piston pump assembly;
a second disposable conduit that places the disposable bubble eliminator in fluid communication with a disposable flow meter;
a second one-way outlet valve disposed in the second disposable conduit between the disposable bubble eliminator and the disposable flow meter and operable to prevent the fluid medium from flowing from the disposable flow meter to the disposable bubble eliminator; and
a reusable component comprising:
a reusable movable stage operable to compress the disposable piston pump assembly;
a reusable mechanical actuator operable to drive the movable stage;
a reusable reception tunnel configured to receive at least a portion of the first disposable conduit;
a reusable inlet valve operable to close the first disposable conduit when the at least a portion of the first disposable conduit is disposed in the reusable reception tunnel;
a reusable flow meter connector operable to connect to the disposable flow meter and to convey data from the disposable flow meter; and
a reusable bubble detector.

2. The pump of claim 1, wherein the reusable inlet valve is a one-way valve or a pinch valve.

3. The pump of claim 1, wherein the disposable piston pump assembly comprises:
a piston barrel comprising:
a pump chamber in fluid communication with the first disposable conduit;
a plunger slidably disposed within the piston barrel below the pump chamber;
a piston rod attached to the plunger opposite the pump chamber;
a spring cap attached to the piston rod; and
a spring disposed around an exterior of the piston barrel and attached at an upper end of the spring to the exterior of the piston barrel and at a lower end of the spring to the spring cap, wherein the spring is disposed to store energy when the plunger, the piston rod, and the spring cap are moved into the piston barrel and is disposed not to store energy when the plunger is at the lower end of the pump chamber;
wherein the reusable movable stage is disposed to move the plunger upward in the piston barrel and the spring is disposed to move the plunger downward in the pump chamber.

4. The pump of claim 1, wherein the disposable bubble eliminator is in fluid communication with the disposable piston pump assembly and the disposable flow meter and comprises a vent through which gas in the fluid medium may escape the disposable bubble eliminator to the atmosphere when pressure higher than atmospheric pressure is maintained in the disposable bubble eliminator.

5. The pump of claim 1, wherein the disposable component further comprises a disposable position measurement device to detect an alignment of the disposable component with the reusable component when assembled together.

6. The pump of claim 1, wherein the reusable bubble detector comprises:
a reusable bubble detector conduit in fluid communication with the disposable component outlet port when the disposable component and the reusable component are assembled together; and
a reusable ultrasonic sensor to detect gas in the fluid medium, disposed outside the reusable bubble detector conduit.

7. The pump of claim 1, wherein the reusable component further comprises at least one of:
an internal electric battery or electrical connections configured to connect to an external electrical power source or both;
an internal power management system or power management connections configured to connect to an external power management system or both;
an integral control panel or control panel connections configured to connect to an external control panel or both;
a screen interface or screen interface connections configured to connect to an external screen interface or both; or
a disposable housing or the reusable component or both are disposed in a reusable housing.

8. A kit comprising:
a disposable component comprising:
a disposable component inlet port coupled to a first disposable conduit in fluid communication with a fluid medium source, wherein the first disposable conduit comprises a disposable piston pump assembly and a disposable bubble eliminator, and the first disposable conduit is in fluid communication with a disposable component outlet port, wherein the disposable bubble eliminator is in fluid communication with a lumen of the first disposable conduit and is operable to reduce a gas content of a fluid medium;
wherein the disposable piston pump assembly comprises a plunger in direct contact with the fluid medium, and wherein the disposable piston pump assembly is operable to pump the fluid medium from the disposable component inlet port, through the first disposable conduit and the disposable bubble eliminator, to the disposable component outlet port;
a first one-way outlet valve disposed in the first disposable conduit between the piston assembly and the disposable bubble eliminator and operable to prevent the fluid medium from flowing from the disposable bubble eliminator to the disposable piston pump assembly;
a second disposable conduit that places the disposable bubble eliminator in fluid communication with a disposable flow meter;
a second one-way outlet valve disposed in the second disposable conduit between the disposable bubble eliminator and the disposable flow meter and operable to prevent the fluid medium from flowing from the disposable flow meter to the disposable bubble eliminator; and
a reusable component comprising:
a reusable movable stage operable to compress the disposable piston pump assembly;
a reusable mechanical actuator operable to drive the movable stage;
a reusable reception tunnel configured to receive at least a portion of the first disposable conduit;
a reusable inlet valve operable to close the first disposable conduit when the at least a portion of the first disposable conduit is disposed in the reusable reception tunnel;
a reusable flow meter connector operable to connect to the disposable flow meter and to convey data from the disposable flow meter; and
a reusable bubble detector.

9. The kit of claim 8, wherein the reusable inlet valve is a one-way valve or a pinch valve.

10. The kit of claim 8, wherein the disposable piston pump assembly comprises:
a piston barrel comprising:
a pump chamber in fluid communication with the first disposable conduit;
a plunger slidably disposed within the piston barrel below the pump chamber;
a piston rod attached to the plunger opposite the pump chamber;
a spring cap attached to the piston rod; and
a spring disposed around an exterior of the piston barrel and attached at an upper end of the spring to the exterior of the piston barrel and at a lower end of the spring to the spring cap, wherein the spring is disposed to store energy when the plunger, the piston rod, and the spring cap are moved into the piston barrel and is disposed not to store energy when the plunger is at the lower end of the pump chamber;
wherein the reusable movable stage is disposed to move the plunger upward in the piston barrel and the spring is disposed to move the plunger downward in the pump chamber.

11. The kit of claim 8, wherein the disposable bubble eliminator is in fluid communication with the disposable piston pump assembly and the disposable flow meter and comprises a vent through which gas in the fluid medium may escape the disposable bubble eliminator to the atmosphere when pressure higher than atmospheric pressure is maintained in the disposable bubble eliminator.

12. The kit of claim 8, wherein the disposable component further comprises a disposable position measurement device to detect an alignment of the disposable component with the reusable component when assembled together.

13. The kit of claim 8, wherein the reusable bubble detector comprises:
a reusable bubble detector conduit in fluid communication with the disposable component outlet port when the disposable component and the reusable component are assembled together; and
a reusable ultrasonic sensor to detect gas in the fluid medium, disposed outside the reusable bubble detector conduit.

14. The kit of claim 8, wherein the reusable component further comprises at least one of:
an internal electric battery or electrical connections configured to connect to an external electrical power source or both;
an internal power management system or power management connections configured to connect to an external power management system or both;
an integral control panel or control panel connections configured to connect to an external control panel or both;
a screen interface or screen interface connections configured to connect to an external screen interface or both; or
a disposable housing or the reusable component or both are disposed in a reusable housing.

* * * * *